(12) United States Patent
Xu et al.

(10) Patent No.: US 7,288,399 B2
(45) Date of Patent: Oct. 30, 2007

(54) 3'-PHOSPHOADENOSINE-5'-PHOSPHOSULFATE SYNTHETASE 1 (PAPSS1) SEQUENCE VARIANTS

(75) Inventors: Zhenhua Xu, Bridgewater, NJ (US); Eric D. Wieben, Rochester, MN (US); Richard M. Weinshilboum, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 10 days.

(21) Appl. No.: 11/416,116

(22) Filed: May 2, 2006

(65) Prior Publication Data

US 2006/0188973 A1    Aug. 24, 2006

Related U.S. Application Data

(62) Division of application No. 10/294,229, filed on Nov. 14, 2002, now Pat. No. 7,067,311.

(60) Provisional application No. 60/332,690, filed on Nov. 14, 2001.

(51) Int. Cl.
    *C12N 9/12*     (2006.01)
(52) U.S. Cl. .................................................. 435/194
(58) Field of Classification Search .................... None
    See application file for complete search history.

(56) References Cited

U.S. PATENT DOCUMENTS

| | | | |
|---|---|---|---|
| 5,451,683 | A | 9/1995 | Barrett et al. |
| 5,733,729 | A | 3/1998 | Lipshutz et al. |
| 5,770,722 | A | 6/1998 | Lockhart et al. |
| 5,817,482 | A | 10/1998 | Bandman et al. |
| 6,525,174 | B1 | 2/2003 | Young et al. |
| 6,699,703 | B1 | 3/2004 | Doucette-Stamm et al. |
| 6,812,339 | B1 | 11/2004 | Venter et al. |

FOREIGN PATENT DOCUMENTS

| | | |
|---|---|---|
| WO | WO 98/20019 | 5/1998 |
| WO | WO 99/57318 | 11/1999 |

OTHER PUBLICATIONS

GenBank Accession No. AC004045 dated Feb. 4, 1998, 31 pages.
GenBank Accession No. AF091242 dated Oct. 20, 1998, 2 pages.
GenBank Accession No. AF097710 dated Mar. 9, 2000, 3 pages.
GenBank Accession No. AF097711 dated Mar. 9, 2000, 2 pages.
GenBank Accession No. AF097712 dated Mar. 9, 2000, 2 pages.
GenBank Accession No. AF097713 dated Mar. 9, 2000, 2 pages.
GenBank Accession No. AF097714 dated Mar. 9, 2000, 2 pages.
GenBank Accession No. AF097715 dated Mar. 9, 2000, 2 pages.
GenBank Accession No. AF097716 dated Mar. 9, 2000, 2 pages.
GenBank Accession No. AF097717 dated Mar. 9, 2000, 2 pages.
GenBank Accession No. AF097718 dated Mar. 9, 2000, 2 pages.
GenBank Accession No. AF097719 dated Mar. 9, 2000, 2 pages.
GenBank Accession No. AF097720 dated Mar. 9, 2000, 2 pages.
GenBank Accession No. AF097721 dated Mar. 9, 2000, 3 pages.
GenBank Accession No. AF105227 dated Mar. 9, 2000, 3 pages.
GenBank Accession No. AF160503 dated Mar. 10, 2000, 3 pages.
GenBank Accession No. AF160504 dated Mar. 10, 2000, 2 pages.
GenBank Accession No. AF160505 dated Mar. 10, 2000, 3 pages.
GenBank Accession No. AF160506 dated Mar. 10, 2000, 2 pages.
GenBank Accession No. AF160507 dated Mar. 10, 2000, 2 pages.
GenBank Accession No. AF160508 dated Mar. 10, 2000, 3 pages.
GenBank Accession No. AF160509 dated Mar. 10, 2000, 3 pages.
GenBank Accession No. BB172819 dated Jun. 29, 2000, 2 pages.
GenBank Accession No. BG476249 dated Mar. 21, 2001, 2 pages.
GenBank Accession No. BI855664 dated Oct. 15, 2001, 2 pages.
Aksoy et al., "Human Liver Estrogen Sulfotransferase: Identification by cDNA Cloning and Expression," *Biochem. Biophys. Res. Commun.*, 1994, 200:1621-1629.
Bradford et al., "A Rapid and Sensitive Method for the Quantitation of microgram Quantities of Protein Utilizing the Principle of Protein-Dye Binding," *Anal. Biochem*, 1976, 72:248-254.
Chadwick et al., "Heterozygote and Mutation Detection by Direct Automated Fluorescent DNA Sequencing Using a Mutant Taq DNA Polymerase," *Biotechniques*, 1996, 20:676-683.
Cibelli et al., "Cloned Transgenic Calves Produced from Nonquiescent Fetal Fibroblasts," *Science*, 1998, 280:1256-1258.
Cleland, "Computer Programmes for Processing Enzyme Kinetic Data," *Nature*, 1963, 198:463-465.
Cote et al., "Generation of human monoclonal antibodies reactive with cellular antigens," *Proc. Natl. Acad. Sci. USA*, 1983, 80:2026-2030.
Cole et al., "The EBV-Hybridoma Technique and its Application to Human Lung Cancer," *Monoclonal Antibodies and Cancer Therapy*, 1985, Alan R. Liss, Inc., pp. 77-96.
Collins et al., "A DNA Polymorphism Discovery Resource for Research on Human Genetic Variation," *Genome Research*, 1998, 8(12):1229-1231.
Excoffier and Slatkin, "Maximum-Likelihood Estimation of Molecular Haplotype Frequencies in a Diploid Population," *Mol. Biol. Evol.*, 1995, 12:921-927.
Flohe et al., "Kinetics of Purified Catechol O-Methyltransferase," *Biochim. Biophys. Acta*, 1970, 220:469-476.
Gordon et al., "Consed: A Graphical Tool for Sequence Finishing," *Genome Res.*, 1998, 8:195-202.
Guatelli et al., "Isothermal, in vitro amplification of nucleic acids by a multienzyme reaction modeled after retroviral replication," *Proc. Natl. Acad. Sci. USA*, 1990, 87:1874-1878.
Hacia et al., "Detection of heterozygous mutations in BRCA1 using high density oligonucleotide arrays and two-colour fluorescence analysis," *Nature Genet.*, 1996, 14:441-447.
Halushka et al., "Patterns of single-nucleotide polymorphisms in candidate genes for blood-pressure homeostasis," *Nature Genet.*, 1999, 22:239-247.
Hartl and Clark, "Chromosomes and Heredity," *Principles of Population Genetics*, 3rd Edition, 1997, Sinauer Associates, Inc., Sunderland, MA, pp. 96-106.

(Continued)

*Primary Examiner*—James Martinell
(74) *Attorney, Agent, or Firm*—Fish & Richardson P.C.

(57) ABSTRACT

Isolated PAPSS1 nucleic acid molecules that include a nucleotide sequence variant and nucleotides flanking the sequence variant are described, as well as PAPSS1 allozymes. Methods for determining if a mammal is predisposed to joint disease or cancer also are described.

3 Claims, 9 Drawing Sheets

OTHER PUBLICATIONS

Hedrick, "An Introduction to Gametic Disequilibrium," *Genetics of Populations*, 2nd Edition, 2000, Jones and Bartlett, Sudbury, MA, pp. 396-405.

Huse et al., "Generation of a Large Combinatorial Library of the Immunoglobulin Repertoire in Phage Lambda," *Science*, 1989, 246:1275-1281.

Hyrup and Nielsen, "Peptide Nucleic Acids (PNA): Synthesis, Properties and Potential Applications," *Bioorgan. Med. Chem.*, 1996, 4(1):5-23.

Klaassen and Boles, "The importance of 3'-phosphoadenosine 5'-phosphosulfate (PAPS) in the regulation of sulfation," *FASEB J.*, 1997, 11:404-418.

Köhler and Nielsen, "Continuous cultures of fused cells secreting antibody of predefined specificity," *Nature*, 1975, 256:495.

Kozbor and Roder, "The production of monoclonal antibodies from human lymphocytes," *Immunology Today*, 1983, 4:72-79.

Kurima et al., "A member of a family of sulfate-activating enzymes causes murine brachymorphism," *Proc. Natl. Acad. Sci. USA*, 1998, 95:8681-8685.

Lewis, "PCR's Competitors Are Alive and Well and Moving Rapidly Towards Commercialization," *Genetic Engineering News*, 1992, 12(9):1-3.

Long et al., "An E-M Algorithm and Testing Strategy for Multiple-Locus Haplotypes," *Am. J. Hum, Genet.*, 1995, 56:799-810.

Myakishev et al., "High-Throughput SNP Genotyping by Allele-Specific PCR with Universal Energy-Transfer-Labeled Primers," *Genome Research*, 2001, 11(1):163-169.

Nickerson et al., "PolyPhred: automating the detection and genotyping of single nucleotide substitutions using fluorescence-based resequencing," *Nucl. Acids Res.*, 1997, 25:2745-2751.

Price et al., "Robust and Accurate Single Nucleotide Polymorphism Genotyping by Dynamic Allele-Specific Hybridization (DASH): Design Criteria and Assay Validation," *Genome Res.*, 2001, 11(1):152-162.

Schafer et al., "DNA variation and the future of human genetics," *Nat. Biotechnol.*, 1998, 15:33-39.

Shastry, "Gene disruption in mice: Models of development and disease," *Mol. Cell. Biochem.*, 1998, 181(1-2):163-179.

Stephens et al., "Haplotype Variation and Linkage Disequilibrium in 313 Human Genes," *Science*, 2001, 293:489-493.

Stoneking et al., "Population Variation of Human mtDNA Control Region Sequences Detected by Enzymatic Amplification and Sequence-specific Oligonucleotide Probes," *Am. J. Hum. Genet.*, 1991, 48:370-382.

Summerton and Weller, "Morpholino Antisense Oligomers: Design, Preparation, and Properties," *Antisense Nucleic Acid Drug. Dev.*, 1997, 7(3):187-195.

Terwilliger and Ott, "Linkage Disequilibrium between Alleles at Marker Loci," *Handbook of Human Genetic Linkage*, 1994, The Johns Hopkins University Press, Baltimore, pp. 188-193.

Tilgmann and Kalkkinen, "Purification and partial characterization of rat liver soluble catechol-o-methyltransferase," *FEBS Lett.*, 1990, 264:95-99.

ul Haque et al., "Mutations in orthologous genes in human spondyloepimetaphyseal dysplasia and the brachymorphic mouse," *Nature Genet.*, 1998, 20(2):157-162.

Underhill et al., "Detection of Numerous Y Chromosome Biallelic Polymorphisms by Denaturing High-Performance Liquid Chromatography," *Genome Res.*, 1997, 7:996-1005.

Venkatachalam et al., "Molecular Cloning, Expression, and Characterization of Human Bifunctional 3'-Phosphoadenosine 5'-Phosphosulfate Synthase and Its Functional Domains," *J. Biol. Chem.*, 1998, 273:19311-19320.

Wakayama et al., "Full-term development of mice from enucleated oocytes injected with cumulus cell nuclei," *Nature*, 1998, 394(6691):369-374.

Weiss, "Hot Prospect for New Gene Amplifier," *Science*, 1991, 254:1292.

Wilkinson et al., "Statistical Estimations in Enzyme Kinetics," *Biochem. J.*, 1961, 80:324-332.

Wilmut et al., "Viable offspring derived from fetal and adult mammalian cells," *Nature*, 1997, 385(6619):810-813.

Wong et al., "Human GM-CSF: Molecular Cloning of the Complementary DNA and Purification of the Natural and Recombinant Proteins," *Science*, 1985, 228:810-815.

Wood et al., "Human Liver Thermolabile Phenol Sulfotransferase: cDNA Cloning, Expression and Characterization," *Biochem. Biophys. Res. Commun.*, 1994, 198:1119-1127.

Xu et al., Human 3'-Phosphoadenosine 5'-Phosphosulfate Synthetase 1 (PAPSS1) and PAPSS2 Gene Cloning, Characterization and Chromosomal Localization, *Biochem. Biophys. Res. Commun.*, 2000, 268:437-444.

Xu et al., "Human 3'-Phosphoadenosine 5'-Phosphosulfate Synthetase: Radiochemical Enzymatic Assay, Biochemical Properties, and Hepatic Variation," *Drug Metab. Dispos.*, 2001, 29(2):172-178.

Xu et al., "Human 3'-phosphoadenosine 5'phosphosulfate synthetase 2 (PAPSS2) pharmacogenetics: gene resequencing, genetic polymorphisms and functional characterizaition of variant allozymes," *Pharmacogenetics*, 2002, 12:11-21.

FIGURE 1 – page 1 tgctagtcactaacaggcagcagcctcaggtcttggtgatgggggctgatttgctagtca
ctaacaggcagcagcagcagcctcaggtcttggtgatgggggctaatttgctagtcacta
acaggcagcagtctcaggtcttggtgatgggcggggtcaggggcggagggcggctgtgtc
acagggggcagagctgcaagcaactcttttggtgccaggggcaagctgcggaaaagaga
actcagagttatgggggtgtggggaagataactcctggaggaaactctgtcatgccccc
agcccatcctcctacgaactagccctggaataattaggtgaatttgaaaatgtcctccgt
aggcgggagttctattcggggttacctgcggcctccccggtcctggatttcagtcctcta
ggtatttcctgagtagctcttaataatacagaagccccttccggtgtaggtcggtaaga
agcactgcacagaaatctgatgcgaagtggggtctcctagcggagagggaggcaccttat
aagtaatcactaatccaggttgagatattaattattgatgtcaagaaatcgggctttat
tatatctttttaaaaactgtgtcttgaggccaggcgctgtcgctcacgcctggaatccca
gcactttgggaagctgaggcgggcggatcatgaggtcaggaattcgagaccagcctggcc
aacatagtgaaaccccgtctctactaaaaatacaaaaattagccgggcgtggtggcacac
gcctgtagtcccagctactcgggaggctgaggcaggagaatcgcttgaacccgggaggca
gaggttgcggtgagccgagatcctactactgcactccagcctgggcgacagagcaagact
ccgtctcaaaaaagaaaaaaaattgtgtcttgagtagaattttaatgtggagaatgagc
tgttcggtaaatcaattcttccctttgcaaagctgtaaaacatttaaaacatttggccag
ggtgacatgggcacagaaggggcagacaggaggtcggcagccaggtctgtggaggagtag
ccagaggtgcaggaggccgcgtcagcgtcctcccaatcagcctctgctgagggagtgccg
cgcgcggcgagccgcgcactccccttgcctttctcccggcggctggtactcgctcttaga
gatctgcgttagctcagagctaggctcggtgccgcagaggcacctgaggttccacgactg
cattccaggccccgccccttcatcgggatctggaaggaggagcgccgtgcgcgcccgcgc
cggcgcgagcgttgaagctccgccccagcttctacctccggttctatcccggcgtttcg
cccttccccacagacctctgccccggacccatttccgaggcgcgccgcatgcgccgcgca
acccaggccacgagcacgggcgcgtgcgcaagtcagcgcgcgcccgctccgacgcgagga
ggccccgccctccagccccgcccgctcgctggcctgCCCTCCTCTTGCTACCCTCCCGG
CGCAGAGAACCCCGGCTGCTCAGCGCGCTCCGCGGTCATGGAGATCCCCGGGAGCCTGTG    Exon 1
CAAGAAAGTCAAGCTGAGCAATAACGCGCAGAACTGGgtaagctggggacgaaggcgaga
cggcgaggagcggaggggctgtgggagcagctcgttccggagccgccgcctctctcccgc
ctcctccgcatccatccttccagcagcgcggaggtgggttccggggctgcggcgcctccc
ggctggggccgtgtgtggttgcgaggcagaggggcgcggcgcagggtggggatctcgccc
tagcttggcgcagcgtgcggtccgagccaccgttcgttggaagaacgcccccctcccca
gcgcctccgctcaggtaagacccccaggaaaatccttcacccgtgaactggcgcttgctg
aaacctccgggtgctgaaaccttgcggctgcagaaacaggagcttcctgcataccttgga
gtggcctgaaagatctgcagagaaggcggaggcnggcgccttcgacgcgttcttggtttt
tcttggctctgcantgcggntggnccaagtttgggtcatctccgtgtctttncatttctg
aatttcagtgtgaaagg        (SEQ ID NO:1)
tgggagtctactcaaatgtcaccttcttagcatgtcttgattatcctctctaaagaggca
ctctgtttccttttttaccctatgttattttttctacagtgcacttatcactctctgatgt
tgtagttaagttttattggtttacattgttccccagtgggatgtaagctaattgagggta
gtgaccttgttttgctcacatggcatactagtagggcctcagtagatactatctgaatgg
atgaacgaataaatgaatgtgtgaaaggactaggctctggagtctgccactcactagttt
tgggatctccggcaagttatttaccattttttcagatttaaaatcttcatctgtaaaacct
tagtagtaagagtacctatgtcattggattgctgtgaggattaaatcagttggcatgtgg

FIGURE 1 – page 2 aaagcagtaaacaccatgccagtactctaaggaaaaaaaaaaactgttttatcttttct
ttgcttttggcatgttacatagacttttgtgtgtttgcaaggaatatgtgtttgccttt
aaaggactcat(a)taaactagaatttttttttttcttttttttctagGGAATGCAGAGAGCA
ACCAATGTCACCTACCAAGCCCATCATGTCAGCAGGAACAAGAGAGGTCAGGTGGTGGGG     Exon 2
ACCAGAGGTGGCTTTCGTGGTTGCACAGTTTGGCTAACAGgtatggtcaagagagagaaa
gcagtttattttaaaagcagtgcatataggtaa(c)ctggactaggcgtaagcatatttaa
attttaagctctgttcttgtatttggagcatcacgacatataactgacatagttgcttaa
taatatttcttgttatttttttttttgttctttataggattgctgttaaataaaggtaa
aaaccacaatgaaccttaaaactacttttttcatagatagcacattaaattctacacactt
ctgagtgcaaataagatctggattctgctctgagaagctaacagtgaaaaccatacgtct
tagtctattttatgctgttataacagaataccagagactgggtaatttatatgaatagaa
atttatttctcatagttctggaggctgggaagtccaagattgagggactagcatcttctt
gctatgtttg (SEQ ID NO:2)
aatattagataagaacattactgagagattgctttgcataatgaatgtatttaatcctgt
gattgcaatttttttatatctcttgagccaggagtttgagaccagctggcgcaacatattg
agaattctgtctctacaaataataaaataagttggatgtggtggcatgtgcctgttgtcc
tagctatttggaaggctgaggcatgatctcttgagtccaggagtttgaggctgcagtgag
ctatgcagcctctgcactccagcctgggtggcagagcaagactcttgtttctgggaaaaa
aaagtattactacatagttatccttctaactttacacatggaatctgtttggactgttta
attttagGCTTGTCTGGAGCGGGAAAGACTACTGTGAGCATGGCCTTGGAGGAGTACCTG
GTTTGTCATGGTATTCCATGCTACACTCTGGATGGTGACAATATTCGTCAAGGTCTCAAT
AAAAATCTTGGCTTTAGTCCTGAAGACAGAGAAGAGAATGTTCGACGCATCGCAGAAGTT     Exon 3
GCTAAACTGTTTGCAGATGCTGGCTTAGTGTGCATCACAAGTTTCATATCACCTTACACT
CAGgtatgtggtttttgtgccattgcctttctgctta(ga)tttattgagaatatggtatca
ggcaaagcacatactttaaacattgatatgtgctttgaggctaactctactcctccccag
ctaccatctctttgttcctgtaacataggattaaaataacctaaaacatttctatgctgt
gacttctaagtaaatctggttttgataaaacctgcttttaaaaaagccgtgaagtataa
cacagtcattgaatttaagccaatggccaaattatttcaggctcaacttttcaacttaat
aaacctatagtgaatacttgacagatgtcaaactccggagaaaatctaactttcttaaca
tgtgccctaccatggcttctttgctcagaattcgttgntcttagcttgcatcatagttcc
tcttatttagagactgcagcaacaacaaaccatgtttg (SEQ ID NO:3)
ggttagtagaacagtatgccttttaaaattgtcatgaataataggaattaacctaataat
ttcttggattttttttttcagtttatatttaaaaacataaattttgtctatttcccactaa
attggatgagaagcacttttttactcatctcttaatattaatatagtacgtttgtgatttgt
gtgatcacttttatttttattttttttaagGATCGCAACAATGCAAGGCAAATTCATGA
AGGTGCAAGTTTACCGTTTTTTGAAGTATTTGTTGATGCTCCTCTGCATGTTTGTGAACA     Exon 4
GAGGGATGTCAAAGGACTCTACAAAAAAGCCCGGGCAGGAGAAATTAAAGgtcagtaata
ttttctt(c)ccagtttcactttgcttagatattttatgttcccatatctaggattgatatt
ttctaagagattggagtgacttggagctccttgaggagagaatgtagtcttattacactg
(9 bp insertion: agtgttaga)

ttctatctctcaggcatagcagcagtgcctggtgctggactaaatgagtcttgttgatcc
ttttggaatcctgttcactagccagagttggggctcgggagttggcgaaaacctacttga

FIGURE 1 – page 3

```
taaaattaggtgcctaacattaagttggacatcagttgcctgctgccaccaattctactt
tctttgttccagggaaaatggaggaaatcccatagctattggaaaaaatgcctgaattat
aagcatcttgatgataaggataatgccttgnactttattacgatccttggaatggtccct
tattcatttcatgtactattgntgaattagattgaattaacatatcactgattctgntaa
aatatatacagctgaccctncacatctgtgcattccacatgtgtgggttcaacccaaccg
tgaattgcatatattccagaagaa    (SEQ ID NO:4)
cacagttcccagcgaaaataaccaaggcagcactttgccttctggttttagttctcaaac
cataancaattattcttttttgcagcctatttggtgtcacattttttacattttttgtggta
ttttaggtagttttacagtttaaaatggcccccagtgcaggaaaaaaaaaagtttaatta
gaaatctcccaagaaagatgcttcattactatagccctgtggcttggggacagcgcaga
tactaacttcaatgtagcagagatctgcactgaaaaaataaactatttttaattttatttt
ccaccctactctattatctgttaccttttgcagGTTTCACTGGGATCGATTCTGAATATG
AAAAGCCAGAGGCCCCTGAGTTGGTGCTGAAAACAGACTCCTGTGATGTAAATGACTGTG       Exon 5
TCCAGCAAGTTGTGGAACTTCTACAGGAACGGgtaagagaggatgaaagaaggaatcatc
agagaaaaattatatctctctcataatctttccctccaaaaaaaaatggtggtgttaat
attgagtaacatttgtatttaaatgcttcgaaatgccaacagtgttctgtgtctgtatg
tcagtgtgtgaggtgttgtggggagcaccgtgaatgtacagtatgtgaaatatcccgtc
agtataaacctcaggaggcttaggagtcagtcttgtactttaccagtaattttgccacag
aaaaatacctaacagaaaatccagccatgattgttcagtcctgtaacttgatagtattat
attttccatttgaggtat    (SEQ ID NO:5)
aaattccagnctggcatttcgtgtgggatcaaaaagttctnattttcaanccacagtggt
gaaagtaaagctgacattctagaatnccgtgttgcttgggtaaaaggtggctttcctgac
agtggtgataaaggtatatataaaagctggaataaaatggtttcgtgatatggtaaagat
aataaggatgatggttcaggtggttttgtttgcttgtttccaaattcttttttgttgtta
cctcttatttgaggccacctctcatttgtagttgcctgactttgacatatgtagtatatt
ttaggaatttattctttcccactagataatgggacattgggcttaattacttcttggatg
tgggatactatctgcttgagagtattggttgaggggaacatagcactcacagccttcttt
tatgctacttttttggttttatttttgagagattttcttcattaagatacccttttggtgaac
tctaaattcttgaatcaaacatttaaattgtactcctgttgttatatagGATATTGTACC
TGTGGATGCATCTTATGAAGTAAAAGAACTATATGTGCCAGAAAATAAACTTCATTTGGC      Exon 6
AAAAACAGATGCGGAAACATTACCAGCACTGAAAATTAATAAAgtaagttcttcgttgct
tttcacactaagtgatacagccttatatacagtagtttgttaaatttgtgacttatagca
gtatttgaggccaggggtggtattagctgggggggcaaagatgttgtggtatatgtcacaa
tttctaaggatggggaatgtgtttaatttgtgcaaccatgttcccaagttaccatggctt
tgatttgctttgagtaataatacttatttattttgaactatcaaagaacaaatattacat
gagatccttaggcttatcagaaataatgggttctaaaaggtcaaggaatactaatccata
gtaattaagtaaacattctccccttcagacatgttttctaatcccttgccaaaacttgac
tctctctgtcttatattgttaagaataatttattgtgtatcttagctctgatgatatca
ttagctgtctttcccaatacaactgcgtagtta    (SEQ ID NO:6)
gggccccacagcaaactgactgaatttgaaactctgcagatgaagcagtctcattttagc
aagctttccaggggtttgaggtaaagtttgagaaccactagtttagganaggctgtcttt
attagaaatacttggaggcctaatgttatttaaatttaataggagaaggaaatattttcc
tagtgcccttattctttgttagtttggtataatctatactcatccttacactgtttgttt
ccattgctttcaaaattaaattcctaaaggtcatcactgcttttgctcatatatacatgc
```

FIGURE 1 – page 4

```
aatagaaaattttgctttactttcaaatttactagGTGGATATGCAGTGGGTGCAGGTTT
TGGCAGAAGGTTGGGCAACCCCATTGAATGGCTTTATGAGAGAGAGGGAGTACTTGCAGT      Exon 7
GCCTTCATTTTGATTGTCTTCTGGATGgtaagacattttacattcaaaattatattgtat
gtggaagagaaattacatagttgcagagatttgtcactgtttacaaaaagtagtagggta
acgtcttaatagaggtagcattataagactaagttatatcagtaccgaacactttattta
agtgaatcatgagatctcattttcgttttccgtgtcctgactcttatttattgcaaaga
gagagggaaaatctgggaatcagggctgaggatggattgtaaaacacatacagttattct
gtgctgnttttgcctgatcactgtggaagctgcttnccacccagggcatgttacgtgct
tgcgttttgcagtctgaacccatgcttgactttctaatga         (SEQ ID NO:7)
tgttaaacagtttgttttacttatgtaattctataccaaaatgttgtacccaaaaacagt
ttgattcttttaattttccttttttttttttttttttaacttgggagatcgttgctcat
tctccctgaccttatagcttgttctgtctttcgttttctgtgccaggtaccagttgaat
actgtcactggatctacagccttttattatttgaaaagtgtccctgaagtgaaaggtgg
gtgttaagtaaagcgtgttgagtaattcaagctgtgtgcttcatgttcttttgtgctctg
cagGAGGTGTCATTAACTTGTCAGTACCTATAGTTCTGACTGCGACTCATGAAGATAAAG
AGAGGCTGGACGGCTGTACAGCATTTGCTCTGATGTATGAGGGCCGCCGTGTGGCCATTC      Exon 8
TTCGCAATCCAGAGTTTTTTGAGCACAGGAAAGAGGAGCGCTGTGCCAGACAGTGGGGAA
CGACATGCAAGAACCACCCCTATATTAAGgtgctgaaaaaacctcgctgcatttatctt
gatttgccaatgatgtttgtgctgaaatgtgggcattttctgtgtattgacttttcattg
gaattgttaatattttgcatagtagagattggaccttagattattgtgatgagtgtttat
gctcttgtcatttggtccagataaatatttattcaacaaacatattttaaatctctatt
gtatacatggcactgagctaggtgctgatgctaggaatgcagggccagggacaccaccgg
cacagtgtttcagctcttggagtatacaatctcgtcgtgtgcttaggcatgtacttataa
tgagccgtgtgaggtagaggctaagggagccctcaccagggtggtttgatgtgaaagcag
tgaaatataattt    (SEQ ID NO:8)
catgatttgtatcgaactcgatgatcattaattcttcaaaaggttaggattggagaacac
agtgtggggtgacccagagctacaaattgttctgttaataaatgtatgataataacgaaa
agaatgttttttgttacttgaaaaggtgtaattattcgcattgcttttgtttgcctttcat
atgtaaagatagttatttcacaagttttctgggaaatcacaaaatcgattctaattttat
agcatctctaatgtcaatttagttgataagtcagatttacctcatttaagatgagagtag
cttacaacgactgtatttagcttatatgagagaaatgtttttacttattttgatctcggt
ttccattaaaaaaatttgttttttcctattagATGGTGATGGAACAAGGAGATTGGCTGAT
TGGAGGAGATCTTCAAGTCTTGGATCGAGTTTATTGGAATGATGGTCTTGATCAGTATCG      Exon 9
TCTTACTCCTACTGAGCTAAAGCAGAAATTTAAAGATATGAATGCTGgtaagacatggat
ttaattacctaatataggccggcttggagagaaagttctagacgattttttccagtgctt
acgaaaatgtaaaacgatgagtacaggtaaatatagcagtggaatatgtaaagaaggta
gtcaatcaaaactagcctgggtagtttcattatattggtataatttgatttgacattatt
ttgaatactctggaagctagatgctaatgcagaatttacctttatttattataaaactc
gcatgttaaagctgaatggaactatagaatattatttggaataattcactcatataaata
tgcttatatg    (SEQ ID NO:9)
aatgatggctctcatttccccatgaatgcaagaaagtaattcttataaatccatgattgt
tatagtacatatcctcagataagtatgatttacttaatattgtatagtagaagtataggt
catgttatcctaaatggtcaaagcagtactttttttttttttttttaccagttttctg
atttctgagtttgcatatgttttgcttaatcctaagtatcaagttttaagaaaaattgcg
```

FIGURE 1 – page 5 tatcctttggaaagtaatctgttagaaacatgctattcttaactctggaaattctctttt
cagATGCTGTCTTTGCATTTCAACTACGCAACCCAGTGCACAATGGACATGCCCTGTTAA
TGCAGGATACCCATAAGCAACTTCTAGAGAGGGGCTACCGGCGCCCTGTCCTCCTCCTCC   Exon 10
ACCCTCTGGGTGGCTGGACAAAGGATGACGATGTTCCTTTGATGTGGCGTATGAAGCAGC
ATGCTGCAGTGTTGGAGGAAGGAGTTCTGAATCCTGAGACGACAGTGGTGGCCATCTTCC
CATCTCCCATGATGTATGCTGGACCAACTGAGgtagactgcttgtaagattttcactgca
Gcagtgttaaagccactcttactaacacagctagtgtcaccatccgattgcttttcctgt
Gctctgtaggcctgttccaaacatttgttatacatgacattctttcctgctcgttaggga
tattccctggatgctaggggcagccttgagaaaggaaaggtggggagaggtttcacttgc
tcttctgggtcttggtcccagttgtgaagganggggatgttccctgcagacagggctggt
gtggntgggaaggtatgccacaagctcctcttgtaactgctggccacattgcagacacaa
caacaacat    (SEQ ID NO:10)
tccagaagctccttgcagttgcctccctccagggatcagcccattatcctgacttctaac
ctcatatattagattttgagctgtgtaaatggcatctggtagttgtgtaaaatcaaacat
ctagacacatgtatgtttacatatatcttataagtaatacataaatatatatacatatat
atccataaatatttgtggatatatgcttttaatcttttggtttgggggaggtttttgttt
tttgttagttttgtttctggcttcccaggatgatacatctaaatttgttgagatttccta
ccgataatgattttataaaaagcatatgcattattatccacttactatttctaagtaca
tagtcataaaagcaaagttacctaaaatgaaacttttattctagGTCCAGTGGCATTGCA
GAGCACGGATGGTTGCAGGAGCCAACTTTTACATTGTTGGACGAGACCCTGCTGGCATGC
CTCATCCAGAAACAGGGAAGGATCTTTATGAGCCAAGTCATGGTGCCAAAGTGCTGACGA   Exon 11
TGGCCCCTGGTTTAATCACTTTGGAAATAGTTCCCTTTCGAGTTGCAGCTTACAACAAGA
AAAAGAAGCGTATGGACTACTATGACTCTGAACAgtaagtcttacattctctgtacaaat
ctttgaagtacttcgtggtctagctgctcccagggatttagcttattgtctaatctttac
tgatgacaggttttgtggtactcatgtcagagaaaggtaaacccagaaaagtaatttccc
aacattctggaaattagaagtagaaataaaacttgaatctagtttcatggtttcaggaat
tttgttttgaagtctgtaaggacaatattg    (SEQ ID NO:11)
ggtagattgtttccacactgataatcctggctgtgatatgctataattttgcaagatgtt
accctttgggaggaaactggataaagggtacaatggtgactggctatattatttcttacaa
tttcatgtgactctacaatggtctcaataaaaatttcaaaactaatttttttctggttct
aaaaattggtaatattcaatagtggtgttttttgttcagtgacaaatttgaaatgagatt
tatattcacaagtactatgttcagtatttttttttcattaagtttgtctaatatgaacag
aaggaacaaatgcttttaaaaatctaagtttctaaaattatgaaataattttcttttt
tcctctcctttagCCATGAAGACTTTGAATTTATTTCAGGAACACGAATGCGCAAACTTG
CTCGAGAAGGCCAGAAACCACCTGAAGGTTTCATGGCTCCCAAGGCTTGGACCGTGCTGA
CAGAATACTACAAATCCTTGGAGAAAGCTTAGGCTGTTAACCCAGTCACTCCACCTTTGA
CACATTACTAGTAACAAGAGGGGACCACATAGTCTCTGTTGGCATTTCTTTGTGGTGTCT
GTCTGGACATGCTTCCTAAAAACAGACCATTTTCCTTAACTTGCATCAGTTTTGGTCTGC   Exon 12
CTTATGAGTTCTGTTTTGAACAAGTGTAACACACTGATGGTTTTAATGTATCTTTTCCAC
TTATTATAGTTATATTCCTACAATACAATTTTAAAATTGTCTTTTTATATTATATTTATG
CTTCTGTGTCATGATTTTTTCAAGCTGTTATATTAGTTGTAACCAGTAGTATTCACATTA
AATCTTGCTTTTTTTCCCCTTAAAAAAGAAAAAAATTACCAAACAATAAACTTGGCTAG
ACCTTGTTTTGAGGATTTTACAAGACCTTTGTAGCGATTAGATTTTTTTCTACATTGAA
AATAGAAACTGCTTCCTTTCTTCTTTCCAGTCAGCTATTGGTCTTTCCAGCTGTTATAAT

FIGURE 1 – page 6

CTAAAGTATTCTTATGATCTGTGTAAGCTCTGAATGAACTTCTTTACTCAATAAAATTAA
TTTTTTGGCTTCTTAtttatgtgatctattttatattgctttgtttccgtatacccttc
ctccttgtgaaaaagtttctgatggaagagggaaaacgcaggcatcttttattactggaa
tccaatacttagtttctaatactgtattacagtgaaattttgatagcaggagactgtgt
tccattatttacgtgggaaaataataaggcattcttagtccatccaaaaaaagtttctt
tgaatatttctctaatattcttaaaacacctgtataacaatttccaaggatttggaacat
(SEQ ID NO:12)

FIGURE 2A

```
   1  tcttgctacc ctcccggcgc agagaacccc ggctgctcag cgcgctccgc ggtcatggag
  61  atccccggga gcttgtgcaa gaaagtcaag ctgagcaata acgcgcagaa ctggggaatg
 121  cagagagcaa ccaatgtcac ctaccaagcc catcatgtca gcaggaacaa gagaggtcag
 181  gtggtgggga ccagaggtgg ctttcgtggt tgcacagttt ggctaacagg cttgtctgga
 241  gcgggaaaga ctactgtgag catggccttg gaggagtacc tggtttgtca tggtattcca
 301  tgctacactc tggatggtga caatattcgt caaggtctca ataaaaatct tggctttagt
 361  cctgaagaca gagaagagaa tgttcgacgc atcgcagaag ttgctaaact gtttgcagat
 421  gctggcttag tgtgcatcac aagtttcata tcaccttaca ctcaggatcg caacaatgca
 481  aggcaaattc atgaaggtgc aagtttaccg tttttgaag tatttgttga tgctcctctg
 541  catgtttgtg aacagaggga tgtcaaagga ctctacaaaa aagcccggc aggagaaatt
 601  aaaggtttca ctgggatcga ttctgaatat gaaaagccag aggccctga gttggtgctg
 661  aaaacagact cctgtgatgt aaatgactgt gtccagcaag ttgtggaact tctacaggaa
 721  cgggatattg tacctgtgga tgcatcttat gaagtaaaag aactatatgt gccagaaaat
 781  aaacttcatt tggcaaaaac agatgcggaa acattaccag cactgaaaat taataaagtg
 841  gatatgcagt gggtgcaggt tttggcagaa ggttgggcaa ccccattgaa tggctttatg
 901  agagagaggg agtacttgca gtgccttcat tttgattgtc ttctggatgg aggtgtcatt
 961  aacttgtcag tacctatagt tctgactgcg actcatgaag ataaagagag gctggacggc
1021  tgtacagcat ttgctctgat gtatgagggc cgccgtgtgg ccattcttcg caatccagag
1081  ttttttgagc acaggaaaga ggagcgctgt gccagacagt ggggaacgac atgcaagaac
1141  cacccctata ttaagatggt gatggaacaa ggagattggc tgattggagg agatcttcaa
1201  gtcttggatc gagtttattg gaatgatggt cttgatcagt atcgtcttac tcctactgag
1261  ctaaagcaga aatttaaaga tatgaatgct gatgctgtct tgcatttca actacgcaac
1321  ccagtgcaca atggacatgc cctgttaatg caggataccc ataagcaact tctagagagg
1381  ggctaccggc gccctgtcct cctcctccac cctctgggtg gctggacaaa ggatgacgat
1441  gttcctttga tgtggcgtat gaagcagcat gctgcagtgt ggaggaagg agttctgaat
1501  cctgagacga cagtggtggc catcttccca tctcccatga tgtatgctgg accaactgag
1561  gtccagtggc attgcagagc acggatggtt gcaggagcca acttttacat tgttggacga
1621  gaccctgctg gcatgcctca tccagaaaca gggaaggatc tttatgagcc aagtcatggt
1681  gccaaagtgc tgacgatggc ccctggttta atcactttgg aaatagttcc ctttcgagtt
1741  gcagcttaca acaagaaaaa gaagcgtatg gactactatg actctgaaca ccatgaagac
1801  tttgaattta ttttaggaac acgaatgcgc aaacttgctc gagaaggcca gaaaccacct
1861  gaaggtttca tggctcccaa ggcttggacc gtgctgacag aatactacaa atccttggag
1921  aaagcttagg ctgttaaccc agtcactcca cctttgacac attactagta acaagagggg
1981  accacatagt ctctgttggc atttctttgt ggtgtctgtc tggacatgct tcctaaaaac
2041  agaccatttt ccttaacttg catcagtttt ggtctgcctt atgagttctg ttttgaacaa
2101  gtgtaacaca ctgatggttt taatgtatct tttccactta ttatagttat attcctacaa
2161  tacaatttta aaattgtctt tttatattat atttatgctt ctgtgtcatg atttttcaa
2221  gctgttatat tagttgtaac cagtagtatt cacattaaat cttgcttttt tccccttaa
2281  aaaaagaaaa aaattaccaa acaataaact tggctagacc ttgttttgag gattttacaa
2341  gacctttgta gcgattagat tttttttcta cattgaaaat agaaactgct tcctttcttc
2401  tttccagtca gctattggtc tttccagctg ttataatcta aagtattctt atgatctgtg
2461  taagctctga angaacttct ttactcaata aaattaattt tttggcttct taaaaaaaa
2521  aaaaaaaaaa aaaaaaa (SEQ ID NO:13)
```

FIGURE 2B

MEIPGSLCKKVKLSNNAQNWGMQRATNVTYQAHHVSRNKRGQVVGTRGGFRGCTVW
LTGLSGAGKTTVSMALEEYLVCHGIPCYTLDGDNIRQGLNKNLGFSPEDREENVRRIAE
VAKLFADAGLVCITSFISPYTQDRNNARQIHEGASLPFFEVFVDAPLHVCEQRDVKGLYK
KARAGEIKGFTGIDSEYEKPEAPELVLKTDSCDVNDCVQQVVELLQERDIVPVDASYEV
KELYVPENKLHLAKTDAETLPALKINKVDMQWVQVLAEGWATPLNGFMREREYLQCL
HFDCLLDGGVINLSVPIVLTATHEDKERLDGCTAFALMYEGRRVAILRNPEFFEHRKEER
CARQWGTTCKNHPYIKMVMEQGDWLIGGDLQVLDRVYWNDGLDQYRLTPTELKQKF
KDMNADAVFAFQLRNPVHNGHALLMQDTHKQLLERGYRRPVLLLHPLGGWTKDDDV
PLMWRMKQHAAVLEEGVLNPETTVVAIFPSPMMYAGPTEVQWHCRARMVAGANFYI
VGRDPAGMPHPETGKDLYEPSHGAKVLTMAPGLITLEIVPFRVAAYNKKKKRMDYYDS
EHHEDFEFILGTRMRKLAREGQKPPEGFMAPKAWTVLTEYYKSLEKA (SEQ ID NO:14)

SEQUENCE LISTING

```
<160> NUMBER OF SEQ ID NOS: 42

<210> SEQ ID NO 1
<211> LENGTH: 2177
<212> TYPE: DNA
<213> ORGANISM: Homo sapiens
<220> FEATURE:
<221> NAME/KEY: misc_feature
<222> LOCATION: 2074, 2114, 2120, 2124, 2152
<223> OTHER INFORMATION: n = A,T,C or G

<400> SEQUENCE: 1
tgctagtcac taacaggcag cagcctcagg tcttggtgat gggggctgat ttgctagtca      60
ctaacaggca gcagcagcag cctcaggtct tggtgatggg ggctaatttg ctagtcacta     120
acaggcagca gtctcaggtc ttggtgatgg gcggggtcag gggcggaggg cggctgtgtc     180
acaggggggc agagctgcaa gcaactcttt tggtgccagg ggcaagctgc ggaaaagaga     240
actcagagtt atgggggtg tggggaagat aactcctgga ggaaactctg tcatgccccc      300
agcccatcct cctacgaact agccctggaa taattaggtg aatttgaaaa tgtcctccgt     360
aggcgggagt tctattcggg gttacctgcg gcctccccgg tcctggattt cagtcctcta     420
ggtatttcct gagtagctct taataataca gaagcccctt tccggtgtag gtcggtaaga     480
agcactgcac agaaatctga tgcgaagtgg ggtctcctag cggagaggga ggcaccttat     540
aagtaatcac taatccaggt tgagatatta attattgatg tcaagaaatc gggcttttat     600
tatatctttt taaaaactgt gtcttgaggc caggcgctgt cgctcacgcc tggaatccca     660
gcactttggg aagctgaggc gggcggatca tgaggtcagg aattcgagac cagcctggcc     720
aacatagtga aaccccgtct ctactaaaaa tacaaaaatt agccgggcgt ggtggcacac     780
gcctgtagtc ccagctactc gggaggctga ggcaggagaa tcgcttgaac ccgggaggca     840
gaggttgcgg tgagccgaga tcctactact gcactccagc ctgggcgaca gagcaagact     900
ccgtctcaaa aaaagaaaaa aaattgtgtc ttgagtagaa ttttaatgtg gagaatgagc     960
tgttcggtaa atcaattctt ccctttgcaa agctgtaaaa catttaaaac atttggccag    1020
ggtgacatgg gcacagaagg ggcagacagg aggtcggcag ccaggtctgt ggaggagtag    1080
```

-continued

```
ccagaggtgc aggaggccgc gtcagcgtcc tcccaatcag cctctgctga gggagtgccg    1140
cgcgcggcga gccgcgcact ccccttgcct ttctcccggc ggctggtact cgctcttaga    1200
gatctgcgtt agctcagagc taggctcggt gccgcagagg cacctgaggt tccacgactg    1260
cattccaggc cccgcccctt catcgggatc tggaaggagg agcgccgtgc gcgcccgcgc    1320
cggcgcgagc gttgaagctc cgcccccagc ttctacctcc ggttctatcc cggcgtttcg    1380
cccttcccca cagacctctg ccccggaccc atttccgagg cgcgccgcat gcgccgcgca    1440
acccaggcca cgagcacggg cgcgtgcgca agtcagcgcg cgcccgctcc gacgcgagga    1500
ggccccgccc tccagccccg ccccgctcgc tggcctgccc tcctcttgct accctcccgg    1560
cgcagagaac cccggctgct cagcgcgctc cgcggtcatg gagatccccg ggagcctgtg    1620
caagaaagtc aagctgagca ataacgcgca gaactgggta agctgggac gaaggcgaga     1680
cggcgaggag cggaggggct gtgggagcag ctcgttccgg agccgccgcc tctctcccgc    1740
ctcctccgca tccatccttc cagcagcgcg gaggtgggtt ccggggctgc ggcgcctccc    1800
ggctggggcc gtgtgtggtt gcgaggcaga ggggcgcggc gcagggtggg gatctcgccc    1860
tagcttggcg cagcgtgcgg tccgagccac cgttcgttgg aagaacgccc ccctccccca    1920
gcgcctccgc tcaggtaaga ccccccaggaa atccttcac ccgtgaactg gcgcttgctg    1980
aaacctccgg gtgctgaaac cttgcggctg cagaaacagg agcttcctgc ataccttgga    2040
gtggcctgaa agatctgcag agaaggcgga ggcnggcgcc ttcgacgcgt tcttggtttt    2100
tcttggctct gcantgcggn tggnccaagt ttgggtcatc tccgtgtctt tncatttctg    2160
aatttcagtg tgaaagg                                                   2177
```

<210> SEQ ID NO 2
<211> LENGTH: 1150
<212> TYPE: DNA
<213> ORGANISM: Homo sapiens

<400> SEQUENCE: 2

```
tgggagtcta ctcaaatgtc accttcttag catgtcttga ttatcctctc taaagaggca      60
ctctgtttcc ttttttaccc tatgttattt ttctacagtg cacttatcac tctctgatgt     120
tgtagttaag ttttattggt ttacattgtt ccccagtggg atgtaagcta attgagggta     180
gtgaccttgt tttgctcaca tggcatacta gtagggcctc agtagatact atctgaatgg     240
atgaacgaat aaatgaatgt gtgaaaggac taggctctgg agtctgccac tcactagttt     300
tgggatctcc ggcaagttat ttaccatttt tcagatttaa aatcttcatc tgtaaaacct     360
tagtagtaag agtacctatg tcattggatt gctgtgagga ttaaatcagt tggcatgtgg     420
aaagcagtaa acaccatgcc agtactctaa ggaaaaaaaa aaactgtttt atcttttct     480
ttgcttttgg catgttacat agacttttgt gtgtttgcaa ggaatatgtg tttgccttt     540
aaaggactca tataaactag aatttttttt ttcttttttt tctagggaat gcagagagca    600
accaatgtca cctaccaagc ccatcatgtc agcaggaaca agagaggtca ggtggtgggg    660
accagaggtg gctttcgtgg ttgcacagtt tggctaacag gtatggtcaa gagagagaaa    720
gcagtttatt ttaaaagcag tgcatatagg taaccttgga ctaggcgtaa gcatatttaa    780
attttaagct ctgttcttgt atttggagca tcacgacata taactgacat agttgcttaa    840
taatatttct tgttattttt tttttgttc tttatagga ttgctgttaa ataaaggtaa     900
aaaccacaat gaaccttaaa actactttt catagatagc acattaaatt ctacacactt    960
ctgagtgcaa ataagatctg gattctgctc tgagaagcta acagtgaaaa ccatacgtct   1020
```

```
tagtctattt tatgctgtta taacagaata ccagagactg ggtaatttat atgaatagaa    1080
atttatttct catagttctg gaggctggga agtccaagat tgagggacta gcatcttctt    1140
gctatgtttg                                                          1150
```

<210> SEQ ID NO 3
<211> LENGTH: 1059
<212> TYPE: DNA
<213> ORGANISM: Homo sapiens
<220> FEATURE:
<221> NAME/KEY: misc_feature
<222> LOCATION: 998
<223> OTHER INFORMATION: n = A,T,C or G

<400> SEQUENCE: 3

```
aatattagat aagaacatta ctgagagatt gctttgcata atgaatgtat ttaatcctgt      60
gattgcaatt ttttatatct cttgagccag gagtttgaga ccagctggcg caacatattg     120
agaattctgt ctctacaaat aataaaataa gttggatgtg gtggcatgtg cctgttgtcc     180
tagctatttg gaaggctgag gcatgatctc ttgagtccag gagtttgagg ctgcagtgag     240
ctatgcagcc tctgcactcc agcctgggtg gcagagcaag actcttgttt ctgggaaaaa     300
aaagtattac tacatagtta tccttctaac tttacacatg gaatctgttt ggactgttta     360
attttaggct tgtctggagc gggaaagact actgtgagca tggccttgga ggagtacctg     420
gtttgtcatg gtattccatg ctacactctg gatggtgaca atattcgtca aggtctcaat     480
aaaaatcttg gctttagtcc tgaagacaga gaagagaatg ttcgacgcat cgcagaagtt     540
gctaaactgt ttgcagatgc tggcttagtg tgcatcacaa gtttcatatc accttacact     600
caggtatgtg gtttttgtgc cattgccttt ctgcttacat ttattgagaa atggtatca     660 ggcaaagcac atactttaaa cattgatatg tgctttgagg ctaactctac tcctccccag     720
ctaccatctc tttgttcctg taacatagga ttaaaataac ctaaaacatt tctatgctgt     780
gactttctaa gtaaatctgg ttttgataaa acctgctttt aaaaaagccg tgaagtataa     840
cacagtcatt gaatttaagc caatggccaa attatttcag gctcaacttt tcaacttaat     900
aaacctatag tgaatacttg acagatgtca aactccggag aaaatctaac tttcttaaca     960
tgtgccctac catggcttct tgctcagaa ttcgttgntc ttagcttgca tcatagttcc    1020
tcttatttta gagactgcag caacaacaaa ccatgtttg                           1059
```

<210> SEQ ID NO 4
<211> LENGTH: 924
<212> TYPE: DNA
<213> ORGANISM: Homo sapiens
<220> FEATURE:
<221> NAME/KEY: misc_feature
<222> LOCATION: 751, 802, 837, 860
<223> OTHER INFORMATION: n = A,T,C or G

<400> SEQUENCE: 4

```
ggttagtaga acagtatgcc ttttaaaatt gtcatgaata ataggaatta acctaataat      60
ttcttggatt ttttttcag tttatattta aaaacataaa ttttgtctat ttcccactaa     120
attggatgag aagcactttt tactcatctt taatattaat atagtacgtt tgtgatttgt     180
gtgatcactt tttattttat tttttttaa ggatcgcaac aatgcaaggc aaattcatga     240
aggtgcaagt ttaccgtttt ttgaagtatt tgttgatgct cctctgcatg tttgtgaaca     300
gagggatgtc aaaggactct acaaaaaagc ccgggcagga gaaattaaag gtcagtaata     360
ttttcttccc agtttcactt tgcttagata ttttatgttc ccatatctag gattgatatt     420
```

-continued

| | |
|---|---|
| ttctaagaga ttggagtgac ttggagctcc ttgaggagag aatgtagtct tattacactg | 480 |
| ttctatctct caggcatagc agcagtgcct ggtgctggac taaatgagtc ttgttgatcc | 540 |
| ttttggaatc ctgttcacta gccagagttg gggctcggga gttggcgaaa acctacttga | 600 |
| taaaattagg tgcctaacat taagttggac atcagttgcc tgctgccacc aattctactt | 660 |
| tctttgttcc agggaaaatg gaggaaatcc catagctatt ggaaaaaatg cctgaattat | 720 |
| aagcatcttg atgataagga taatgccttg nactttatta cgatccttgg aatggtccct | 780 |
| tattcatttc atgtactatt gntgaattag attgaattaa catatcactg attctgntaa | 840 |
| aatatataca gctgaccctn cacatctgtg cattccacat gtgtgggttc aacccaaccg | 900 |
| tgaattgcat atattccaga agaa | 924 |

<210> SEQ ID NO 5
<211> LENGTH: 799
<212> TYPE: DNA
<213> ORGANISM: Homo sapiens
<220> FEATURE:
<221> NAME/KEY: misc_feature
<222> LOCATION: 66
<223> OTHER INFORMATION: n = A,T,C or G

<400> SEQUENCE: 5

| | |
|---|---|
| cacagttccc agcgaaaata accaaggcag cactttgcct tctggtttta gttctcaaac | 60 |
| cataancaat tattctttt gcagcctatt tggtgtcaca tttttacat ttttgtggta | 120 |
| ttttaggtag ttttacagtt taaaatggcc cccagtgcag gaaaaaaaaa agtttaatta | 180 |
| gaaatctccc aagaaagatg cttcattact atagccctgt ggcttggggg acagcgcaga | 240 |
| tactaacttc aatgtagcag agatctgcac tgaaaaaata aactatttta attttatttt | 300 |
| ccaccctact ctattatctg ttaccttttg caggtttcac tgggatcgat tctgaatatg | 360 |
| aaaagccaga ggcccctgag ttggtgctga aaacagactc ctgtgatgta aatgactgtg | 420 |
| tccagcaagt tgtggaactt ctacaggaac gggtaagaga ggatgaaaga aggaatcatc | 480 |
| agagaaaaat tatatctctc tcataatctt tcccctccaa aaaaaaatgg tggtgttaat | 540 |
| attgagtaac atttgtattt taaatgcttc gaaatgccaa cagtgttctg tgtctgtatg | 600 |
| tcagtgtgtg aggtgttgtg gggagcaccg tgaatgtaca gtatgtgaaa tatccccgtc | 660 |
| agtataaacc tcaggaggct taggagtcag tcttgtactt taccagtaat tttgccacag | 720 |
| aaaaatacct aacagaaaat ccagccatga ttgttcagtc ctgtaacttg atagtattat | 780 |
| attttttccat ttgaggtat | 799 |

<210> SEQ ID NO 6
<211> LENGTH: 1113
<212> TYPE: DNA
<213> ORGANISM: Homo sapiens
<220> FEATURE:
<221> NAME/KEY: misc_feature
<222> LOCATION: 10, 41, 50, 86
<223> OTHER INFORMATION: n = A,T,C or G

<400> SEQUENCE: 6

| | |
|---|---|
| aaattccagn ctggcatttc gtgtgggatc aaaaagttct nattttcaan ccacagtggt | 60 |
| gaaagtaaag ctgacattct agaatnccgt gttgctgggg taaaaggtgg ctttcctgac | 120 |
| agtggtgata aaggtatata taaaagctgg aataaaatgg tttcgtgata tggtaaagat | 180 |
| aataaggatg atggttcagg tggttttgt ttgcttgttt ccaaattctt tttgttgtta | 240 |
| cctcttattt gaggccacct ctcatttgta gttgcctgac tttgacatat gtagtatatt | 300 |

```
ttaggaattt attctttccc actagataat gggacattgg gcttaattac ttccttggatg      360 tgggatacta tctgcttgag agtattggtt gaggggaaca tagcactcac agccttcttt      420
tatgctactt tttggtttta ttttgagaga ttttcttcat taagatacccc tttggtgaac    480 tctaaattct tgaatcaaac atttaaattg tactcctgtt gttatatagg atattgtacc      540
tgtggatgca tcttatgaag taaaagaact atatgtgcca gaaaataaac ttcatttggc      600
aaaaacagat gcggaaacat taccagcact gaaaattaat aaagtaagtt cttcgttgct      660
tttcacacta agtgatacag ccttatatac agtagtttgt taaatttgtg acttatagca      720
gtatttgagg ccaggggtgg tattagctgg ggggcaaaga tgttgtggta tatgtcacaa      780
tttctaagga tggggaatgt gtttaatttg tgcaaccatg ttcccaagtt accatggctt      840
tgatttgctt tgagtaataa tacttattta ttttgaacta tcaaagaaca aatattacat      900
gagatcctta ggcttatcag aaataatggg ttctaaaagg tcaaggaata ctaatccata      960
gtaattaagt aaacattctc cccttcagac atgttttcta atcccttgcc aaaacttgac     1020
tctctctgtc ttatattgtt aagaataatt ttattgtgta tcttagctct gatgatatca     1080
ttagctgtct ttcccaatac aactgcgtag tta                                  1113

<210> SEQ ID NO 7
<211> LENGTH: 820
<212> TYPE: DNA
<213> ORGANISM: Homo sapiens
<220> FEATURE:
<221> NAME/KEY: misc_feature
<222> LOCATION: 109, 727, 757
<223> OTHER INFORMATION: n = A,T,C or G

<400> SEQUENCE: 7 gggcccccaca gcaaactgac tgaatttgaa actctgcaga tgaagcagtc tcattttagc      60
aagctttcca ggggtttgag gtaaagtttg agaaccacta gtttaggana ggctgtcttt     120
attagaaata cttggaggcc taatgttatt taaatttaat aggagaagga aatattttcc     180
tagtgccctt attctttgtt agtttggtat aatctatact catccttaca ctgtttgttt     240
ccattgcttt caaaattaaa ttcctaaagg tcatcactgc ttttgctcat atatacatgc     300
aatagaaaat tttgctttac tttcaaattt actaggtgga tatgcagtgg gtgcaggttt     360
tggcagaagg ttgggcaacc ccattgaatg gctttatgag agagagggag tacttgcagt     420
gccttcattt tgattgtctt ctggatggta agacatttta cattcaaaat tatattgtat     480
gtggaagaga aattacatag ttgcagagat ttgtcactgt ttacaaaaag tagtagggta     540
acgtcttaat agaggtagca ttataagact aagttatatc agtaccgaac actttattta     600
agtgaatcat gagatctcat tttcgttttt ccgtgtcctg actcttattt attgcaaaga     660
gagagggaaa atctgggaat cagggctgag gatggattgt aaaacacata cagttattct     720
gtgctgnttt tgcctgatca ctgtggaaag ctgcttncca cccagggcat gttacgtgct     780
tgcgttttgc agtctgaacc catgcttgac tttctaatga                           820

<210> SEQ ID NO 8
<211> LENGTH: 913
<212> TYPE: DNA
<213> ORGANISM: Homo sapiens

<400> SEQUENCE: 8
tgttaaacag tttgttttac ttatgtaatt ctataccaaa atgttgtacc caaaaacagt      60
ttgattcttt taatttttcc tttttttttt tttttttaa cttgggagat cgttgctcat     120
```

-continued

| | |
|---|---|
| tctccctgac cttatagctt gttctgtctt tcgttttcct gtgccaggta ccagttgaat | 180 |
| actgtcactg gatctacagc cttttattat ttgaaaagtg tcccctgaag tgaaggtgg | 240 |
| gtgttaagta aagcgtgttg agtaattcaa gctgtgtgct tcatgttctt ttgtgctctg | 300 |
| caggaggtgt cattaacttg tcagtaccta tagttctgac tgcgactcat gaagataaag | 360 |
| agaggctgga cggctgtaca gcatttgctc tgatgtatga gggccgccgt gtggccattc | 420 |
| ttcgcaatcc agagttttt gagcacagga aagaggagcg ctgtgccaga cagtggggaa | 480 |
| cgacatgcaa gaaccacccc tatattaagg tgctgaaaaa acctcgctgc attttatctt | 540 |
| gatttgccaa tgatgtttgt gctgaaatgt gggcatttc tgtgtattga cttttcattg | 600 |
| gaattgttaa tattttgcat agtagagatt ggaccttaga ttattgtgat gagtgtttat | 660 |
| gctcttgtca ttttggtcca gataaatatt tattcaacaa acatatttta aatctctatt | 720 |
| gtatacatgg cactgagcta ggtgctgatg ctaggaatgc agggccaggg acaccaccgg | 780 |
| cacagtgttt cagctcttgg agtatacaat ctcgtcgtgt gcttaggcat gtacttataa | 840 |
| tgagccgtgt gaggtagagg ctaagggagc cctcaccagg gtggtttgat gtgaaagcag | 900 |
| tgaaatataa ttt | 913 |

<210> SEQ ID NO 9
<211> LENGTH: 850
<212> TYPE: DNA
<213> ORGANISM: Homo sapiens

<400> SEQUENCE: 9

| | |
|---|---|
| catgatttgt atcgaactcg atgatcatta attcttcaaa aggttaggat tggagaacac | 60 |
| agtgtgggt gacccagagc tacaaattgt tctgttaata aatgtatgat aataacgaaa | 120 |
| agaatgtttt tgttacttga aaaggtgtaa ttattcgcat tgcttttgtt tgcctttcat | 180 |
| atgtaaagat agttatttca caagttttct gggaaatcac aaaatcgatt ctaattttat | 240 |
| agcatctcta atgtcaattt agttgataag tcagatttac ctcatttaag atgagagtag | 300 |
| cttacaacga ctgtatttag cttatatgag agaaatgttt ttacttattt tgatctcggt | 360 |
| ttccattaaa aaaatttgtt tttcctatta gatggtgatg gaacaaggag attggctgat | 420 |
| tggaggagat cttcaagtct tggatcgagt ttattggaat gatggtcttg atcagtatcg | 480 |
| tcttactcct actgagctaa agcagaaatt taaagatatg aatgctggta agacatggat | 540 |
| ttaattacct aatataggcc ggcttggaga gaaagttcta gacgattttt tccagtgctt | 600 |
| acgaaaatgt aaaacgatga gtacaggtaa atatagcagt ggaatatgta aagaaaggta | 660 |
| gtcaatcaaa actagcctgg gtagtttcat tatattggta taatttgatt tgacattatt | 720 |
| ttgaatactc tggaagctag atgctaatgc agaatttacc ttttatttat tataaaactc | 780 |
| gcatgttaaa gctgaatgga actatagaat attatttgga ataattcact catataaata | 840 |
| tgcttatatg | 850 |

<210> SEQ ID NO 10
<211> LENGTH: 909
<212> TYPE: DNA
<213> ORGANISM: Homo sapiens
<220> FEATURE:
<221> NAME/KEY: misc_feature
<222> LOCATION: 812, 845
<223> OTHER INFORMATION: n = A,T,C or G

<400> SEQUENCE: 10

| | |
|---|---|
| aatgatggct ctcatttccc catgaatgca agaaagtaat tcttataaat ccatgattgt | 60 |

| | |
|---|---:|
| tatagtacat atcctcagat aagtatgatt tacttaatat tgtatagtag aagtataggt | 120 |
| catgttatcc taaatggtca aagcagtact tttttttttt ttttttttac cagttttctg | 180 |
| atttctgagt ttgcatatgt tttgcttaat cctaagtatc aagttttaag aaaaattgcg | 240 |
| tatcctttgg aaagtaatct gttagaaaca tgctattctt aactctggaa attctctttt | 300 |
| cagatgctgt ctttgcattt caactacgca acccagtgca caatggacat gccctgttaa | 360 |
| tgcaggatac ccataagcaa cttctagaga ggggctaccg gcgccctgtc ctcctcctcc | 420 |
| accctctggg tggctggaca aaggatgacg atgttccttt gatgtggcgt atgaagcagc | 480 |
| atgctgcagt gttggaggaa ggagttctga atcctgagac gacagtggtg gccatcttcc | 540 |
| catctcccat gatgtatgct ggaccaactg aggtagactg cttgtaagat tttcactgca | 600 |
| gcagtgttaa agccactctt actaacacag ctagtgtcac catccgattg cttttctgt | 660 |
| gctctgtagg cctgttccaa acatttgtta tacatgacat tctttcctgc tcgttaggga | 720 |
| tattccctgg atgctagggg cagccttgag aaaggaaagg tggggagagg tttcacttgc | 780 |
| tcttctgggt cttggtccca gttgtgaagg angggatgtt ccctgcagac agggctgggt | 840 |
| gtggntggga aggtatgcca caagctcctc ttgtaactgc tggccacatt gcagacacaa | 900 |
| caacaacat | 909 |

<210> SEQ ID NO 11
<211> LENGTH: 870
<212> TYPE: DNA
<213> ORGANISM: Homo sapiens

<400> SEQUENCE: 11

| | |
|---|---:|
| tccagaagct ccttgcagtt gcctccctcc agggatcagc ccattatcct gacttctaac | 60 |
| ctcatatatt agattttgag ctgtgtaaat ggcatctggt agttgtgtaa aatcaaacat | 120 |
| ctagacacat gtatgtttac atatatctta taagtaatac ataaatatat atacatatat | 180 |
| atccataaat atttgtggat atatgctttt aatcttttgg tttgggggag gttttttgttt | 240 |
| tttgttagtt ttgtttctgg cttcccagga tgatacatct aaatttgttg agatttccta | 300 |
| ccgataatga ttttataaaa agcatatgca tttattatcc acttactatt tctaagtaca | 360 |
| tagtcataaa agcaaagtta cctaaaatga aactttttatt ctaggtccag tggcattgca | 420 |
| gagcacggat ggttgcagga gccaactttt acattgttgg acgagaccct gctggcatgc | 480 |
| ctcatccaga aacagggaag gatctttatg agccaagtca tggtgccaaa gtgctgacga | 540 |
| tggcccctgg tttaatcact ttggaaatag ttcccttttcg agttgcagct acaacaaga | 600 |
| aaaagaagcg tatggactac tatgactctg aacagtaagt cttacattct ctgtacaaat | 660 |
| cttttgaagta cttcgtggtc tagctgctcc cagggattta gcttattgtc taatctttac | 720 |
| tgatgacagg ttttgtggta ctcatgtcag agaaaggtaa acccagaaaa gtaatttccc | 780 |
| aacattctgg aaattagaag tagaaataaa acttgaatct agtttcatgg tttcaggaat | 840 |
| tttgttttga agtctgtaag gacaatattg | 870 |

<210> SEQ ID NO 12
<211> LENGTH: 1380
<212> TYPE: DNA
<213> ORGANISM: Homo sapiens

<400> SEQUENCE: 12

| | |
|---|---:|
| ggtagattgt ttccacactg ataatcctgg ctgtgatatg ctataatttt gcaagatgtt | 60 |
| acctttggga ggaaactgga taaagggtac aatggtgact ggctatatta tttcttacaa | 120 |

-continued

| | |
|---|---|
| tttcatgtga ctctacaatg gtctcaataa aaatttcaaa actaattttt ttctggttct | 180 |
| aaaaattggt aatattcaat agtggtgttt tttgttcagt gacaaatttg aaatgagatt | 240 |
| tatattcaca agtactatgt tcagtatttt tttttcatta agtttgtcta atatgaacag | 300 |
| aaggaacaaa tgcttttaa aaatctaagt ttctaaaatt atgaaataat tttcttttt | 360 |
| tcctctcctt tagccatgaa gactttgaat ttatttcagg aacacgaatg cgcaaacttg | 420 |
| ctcgagaagg ccagaaacca cctgaaggtt tcatggctcc caaggcttgg accgtgctga | 480 |
| cagaatacta caaatccttg gagaaagctt aggctgttaa cccagtcact ccacctttga | 540 |
| cacattacta gtaacaagag gggaccacat agtctctgtt ggcatttctt tgtggtgtct | 600 |
| gtctggacat gcttcctaaa aacagaccat tttccttaac ttgcatcagt tttggtctgc | 660 |
| cttatgagtt ctgttttgaa caagtgtaac acactgatgg ttttaatgta tcttttccac | 720 |
| ttattatagt tatattccta caatacaatt ttaaaattgt cttttatat tatatttatg | 780 |
| cttctgtgtc atgattttt caagctgtta tattagttgt aaccagtagt attcacatta | 840 |
| aatcttgctt ttttccct taaaaaaga aaaaaattac caaacaataa acttggctag | 900 |
| accttgtttt gaggatttta caagaccttt gtagcgatta gatttttttt ctacattgaa | 960 |
| aatagaaact gcttcctttc ttctttccag tcagctattg gtctttccag ctgttataat | 1020 |
| ctaaagtatt cttatgatct gtgtaagctc tgaatgaact tctttactca ataaaattaa | 1080 |
| ttttttggct tcttatttat gtgatctatt ttatattgct ttgtttccgt atacccttc | 1140 |
| ctccttgtga aaaagtttct gatggaagag ggaaaacgca ggcatctttt attactggaa | 1200 |
| tccaatactt agtttctaat actgtattac agtgaaattt ttgatagcag gagactgtgt | 1260 |
| tccattattt tacgtgggaa aataataagg cattcttagt ccatccaaaa aaagtttctt | 1320 |
| tgaatatttc tctaatattc ttaaaacacc tgtataacaa tttccaagga tttggaacat | 1380 |

<210> SEQ ID NO 13
<211> LENGTH: 2537
<212> TYPE: DNA
<213> ORGANISM: Homo sapiens
<220> FEATURE:
<221> NAME/KEY: misc_feature
<222> LOCATION: 2472
<223> OTHER INFORMATION: n = A,T,C or G

<400> SEQUENCE: 13

| | |
|---|---|
| tcttgctacc ctcccggcgc agagaacccc ggctgctcag cgcgctccgc ggtcatggag | 60 |
| atccccggga gcttgtgcaa gaaagtcaag ctgagcaata acgcgcagaa ctggggaatg | 120 |
| cagagagcaa ccaatgtcac ctaccaagcc catcatgtca gcaggaacaa gagaggtcag | 180 |
| gtggtgggga ccagaggtgg ctttcgtggt tgcacagttt ggctaacagg cttgtctgga | 240 |
| gcgggaaaga ctactgtgag catggccttg gaggagtacc tggtttgtca tggtattcca | 300 |
| tgctacactc tggatggtga caatattcgt caaggtctca taaaaatct tggctttagt | 360 |
| cctgaagaca gagaagagaa tgttcgacgc atcgcagaag ttgctaaact gtttgcagat | 420 |
| gctggcttag tgtgcatcac aagtttcata tcaccttaca ctcaggatcg caacaatgca | 480 |
| aggcaaattc atgaaggtgc aagtttaccg tttttgaag tatttgttga tgctcctctg | 540 |
| catgtttgtg aacagaggga tgtcaaagga ctctacaaaa aagcccgggc aggagaaatt | 600 |
| aaaggtttca ctgggatcga ttctgaatat gaaaagccag aggcccctga gttggtgctg | 660 |
| aaaacagact cctgtgatgt aaatgactgt gtccagcaag ttgtggaact tctacaggaa | 720 |
| cgggatattg tacctgtgga tgcatcttat gaagtaaaag aactatatgt gccagaaaat | 780 |

-continued

```
aaacttcatt tggcaaaaac agatgcggaa acattaccag cactgaaaat taataaagtg    840
gatatgcagt gggtgcaggt tttggcagaa ggttgggcaa ccccattgaa tggctttatg    900
agagagaggg agtacttgca gtgccttcat tttgattgtc ttctggatgg aggtgtcatt    960
aacttgtcag tacctatagt tctgactgcg actcatgaag ataaagagag gctggacggc   1020
tgtacagcat ttgctctgat gtatgagggc cgccgtgtgg ccattcttcg caatccagag   1080
tttttttgagc acaggaaaga ggagcgctgt gccagacagt ggggaacgac atgcaagaac   1140
caccccctata ttaagatggt gatgaacaa ggagattggc tgattggagg agatcttcaa   1200
gtcttggatc gagtttattg gaatgatggt cttgatcagt atcgtcttac tcctactgag   1260
ctaaagcaga aatttaaaga tatgaatgct gatgctgtct ttgcatttca actacgcaac   1320
ccagtgcaca atggacatgc cctgttaatg caggataccc ataagcaact tctagagagg   1380
ggctaccggc gccctgtcct cctcctccac cctctgggtg ctggacaaa ggatgacgat   1440
gttcctttga tgtggcgtat gaagcagcat gctgcagtgt tggaggaagg agttctgaat   1500
cctgagacga cagtggtggc catcttccca tctcccatga tgtatgctgg accaactgag   1560
gtccagtggc attgcagagc acggatggtt gcaggagcca acttttacat tgttggacga   1620
gaccctgctg gcatgcctca tccagaaaca gggaaggatc tttatgagcc aagtcatggt   1680
gccaaagtgc tgacgatggc ccctggttta atcactttgg aaatagttcc ctttcgagtt   1740
gcagcttaca acaagaaaaa gaagcgtatg gactactatg actctgaaca ccatgaagac   1800
tttgaattta tttaggaac acgaatgcgc aaacttgctc gagaaggcca gaaaccacct   1860
gaaggtttca tggctcccaa ggcttggacc gtgctgacag aatactacaa atccttggag   1920
aaagcttagg ctgttaaccc agtcactcca cctttgacac attactagta acaagagggg   1980
accacatagt ctctgttggc atttctttgt ggtgtctgtc tggacatgct tcctaaaaac   2040
agaccatttt ccttaacttg catcagttttt ggtctgccctt atgagttctg ttttgaacaa   2100
gtgtaacaca ctgatggttt taatgtatct tttccactta ttatagttat attcctacaa   2160
tacaatttta aaattgtctt tttatattat atttatgctt ctgtgtcatg attttttcaa   2220
gctgttatat tagttgtaac cagtagtatt cacattaaat cttgcttttt ttcccttaa   2280
aaaaagaaaa aaattaccaa acaataaact tggctagacc ttgttttgag gattttacaa   2340
gacctttgta gcgattagat ttttttttcta cattgaaaat agaaactgct tcctttcttc   2400
tttccagtca gctattggtc tttccagctg ttataatcta agtattctt atgatctgtg   2460
taagctctga angaacttct ttactcaata aaattaattt tttggcttct taaaaaaaaa   2520
aaaaaaaaaa aaaaaaa                                                  2537
```

<210> SEQ ID NO 14
<211> LENGTH: 624
<212> TYPE: PRT
<213> ORGANISM: Homo sapiens

<400> SEQUENCE: 14

```
Met Glu Ile Pro Gly Ser Leu Cys Lys Lys Val Lys Leu Ser Asn Asn
 1               5                  10                  15

Ala Gln Asn Trp Gly Met Gln Arg Ala Thr Asn Val Thr Tyr Gln Ala
            20                  25                  30

His His Val Ser Arg Asn Lys Arg Gly Gln Val Val Gly Thr Arg Gly
        35                  40                  45

Gly Phe Arg Gly Cys Thr Val Trp Leu Thr Gly Leu Ser Gly Ala Gly
    50                  55                  60
```

```
Lys Thr Thr Val Ser Met Ala Leu Glu Glu Tyr Leu Val Cys His Gly
 65                  70                  75                  80

Ile Pro Cys Tyr Thr Leu Asp Gly Asp Asn Ile Arg Gln Gly Leu Asn
                 85                  90                  95

Lys Asn Leu Gly Phe Ser Pro Glu Asp Arg Glu Asn Val Arg Arg
                100                 105                 110

Ile Ala Glu Val Ala Lys Leu Phe Ala Asp Ala Gly Leu Val Cys Ile
                115                 120                 125

Thr Ser Phe Ile Ser Pro Tyr Thr Gln Asp Arg Asn Asn Ala Arg Gln
    130                 135                 140

Ile His Glu Gly Ala Ser Leu Pro Phe Phe Glu Val Phe Val Asp Ala
145                 150                 155                 160

Pro Leu His Val Cys Glu Gln Arg Asp Val Lys Gly Leu Tyr Lys Lys
                165                 170                 175

Ala Arg Ala Gly Glu Ile Lys Gly Phe Thr Gly Ile Asp Ser Glu Tyr
                180                 185                 190

Glu Lys Pro Glu Ala Pro Glu Leu Val Leu Lys Thr Asp Ser Cys Asp
    195                 200                 205

Val Asn Asp Cys Val Gln Gln Val Val Glu Leu Leu Gln Glu Arg Asp
210                 215                 220

Ile Val Pro Val Asp Ala Ser Tyr Glu Val Lys Glu Leu Tyr Val Pro
225                 230                 235                 240

Glu Asn Lys Leu His Leu Ala Lys Thr Asp Ala Glu Thr Leu Pro Ala
                245                 250                 255

Leu Lys Ile Asn Lys Val Asp Met Gln Trp Val Gln Val Leu Ala Glu
                260                 265                 270

Gly Trp Ala Thr Pro Leu Asn Gly Phe Met Arg Glu Arg Glu Tyr Leu
    275                 280                 285

Gln Cys Leu His Phe Asp Cys Leu Leu Asp Gly Gly Val Ile Asn Leu
    290                 295                 300

Ser Val Pro Ile Val Leu Thr Ala Thr His Glu Asp Lys Glu Arg Leu
305                 310                 315                 320

Asp Gly Cys Thr Ala Phe Ala Leu Met Tyr Glu Gly Arg Arg Val Ala
                325                 330                 335

Ile Leu Arg Asn Pro Glu Phe Phe Glu His Arg Lys Glu Glu Arg Cys
                340                 345                 350

Ala Arg Gln Trp Gly Thr Thr Cys Lys Asn His Pro Tyr Ile Lys Met
    355                 360                 365

Val Met Glu Gln Gly Asp Trp Leu Ile Gly Gly Asp Leu Gln Val Leu
    370                 375                 380

Asp Arg Val Tyr Trp Asn Asp Gly Leu Asp Gln Tyr Arg Leu Thr Pro
385                 390                 395                 400

Thr Glu Leu Lys Gln Lys Phe Lys Asp Met Asn Ala Asp Ala Val Phe
                405                 410                 415

Ala Phe Gln Leu Arg Asn Pro Val His Asn Gly His Ala Leu Leu Met
                420                 425                 430

Gln Asp Thr His Lys Gln Leu Leu Glu Arg Gly Tyr Arg Arg Pro Val
    435                 440                 445

Leu Leu Leu His Pro Leu Gly Gly Trp Thr Lys Asp Asp Val Pro
450                 455                 460

Leu Met Trp Arg Met Lys Gln His Ala Ala Val Leu Glu Glu Gly Val
465                 470                 475                 480
```

```
Leu Asn Pro Glu Thr Thr Val Val Ala Ile Phe Pro Ser Pro Met Met
                485                 490                 495

Tyr Ala Gly Pro Thr Glu Val Gln Trp His Cys Arg Ala Arg Met Val
            500                 505                 510

Ala Gly Ala Asn Phe Tyr Ile Val Gly Arg Asp Pro Ala Gly Met Pro
        515                 520                 525

His Pro Glu Thr Gly Lys Asp Leu Tyr Glu Pro Ser His Gly Ala Lys
    530                 535                 540

Val Leu Thr Met Ala Pro Gly Leu Ile Thr Leu Glu Ile Val Pro Phe
545                 550                 555                 560

Arg Val Ala Ala Tyr Asn Lys Lys Lys Arg Met Asp Tyr Tyr Asp
                565                 570                 575

Ser Glu His His Glu Asp Phe Glu Phe Ile Leu Gly Thr Arg Met Arg
            580                 585                 590

Lys Leu Ala Arg Glu Gly Gln Lys Pro Pro Glu Gly Phe Met Ala Pro
        595                 600                 605

Lys Ala Trp Thr Val Leu Thr Glu Tyr Tyr Lys Ser Leu Glu Lys Ala
    610                 615                 620
```

<210> SEQ ID NO 15
<211> LENGTH: 18
<212> TYPE: DNA
<213> ORGANISM: Artificial Sequence
<220> FEATURE:
<223> OTHER INFORMATION: Primer

<400> SEQUENCE: 15
tgtaaaacga cggccagt                                                 18

<210> SEQ ID NO 16
<211> LENGTH: 18
<212> TYPE: DNA
<213> ORGANISM: Artificial Sequence
<220> FEATURE:
<223> OTHER INFORMATION: Primer

<400> SEQUENCE: 16
caggaaacag ctatgacc                                                 18

<210> SEQ ID NO 17
<211> LENGTH: 33
<212> TYPE: DNA
<213> ORGANISM: Artificial Sequence
<220> FEATURE:
<223> OTHER INFORMATION: Primer

<400> SEQUENCE: 17
gaggaggaat tcatggagat ccccgggagc ttg                                33

<210> SEQ ID NO 18
<211> LENGTH: 37
<212> TYPE: DNA
<213> ORGANISM: Artificial Sequence
<220> FEATURE:
<223> OTHER INFORMATION: Primer

<400> SEQUENCE: 18
gataaggaat tcttaggaag catgtccaga cagacac                            37

<210> SEQ ID NO 19
<211> LENGTH: 42
<212> TYPE: DNA

<213> ORGANISM: Artificial Sequence
<220> FEATURE:
<223> OTHER INFORMATION: Primer

<400> SEQUENCE: 19
tgtaaaacga cggccagtag ccccgccccg ctcgctggcc tg            42

<210> SEQ ID NO 20
<211> LENGTH: 38
<212> TYPE: DNA
<213> ORGANISM: Artificial Sequence
<220> FEATURE:
<223> OTHER INFORMATION: Primer

<400> SEQUENCE: 20
caggaaacag ctatgaccgc cccagccggg aggcgccg                 38

<210> SEQ ID NO 21
<211> LENGTH: 38
<212> TYPE: DNA
<213> ORGANISM: Artificial Sequence
<220> FEATURE:
<223> OTHER INFORMATION: Primer

<400> SEQUENCE: 21
tgtaaaacga cggccagtgc ttttggcatg ttacatag                 38

<210> SEQ ID NO 22
<211> LENGTH: 39
<212> TYPE: DNA
<213> ORGANISM: Artificial Sequence
<220> FEATURE:
<223> OTHER INFORMATION: Primer

<400> SEQUENCE: 22
caggaaacag ctatgacctc gtgatgctcc aaatacaag                39

<210> SEQ ID NO 23
<211> LENGTH: 41
<212> TYPE: DNA
<213> ORGANISM: Artificial Sequence
<220> FEATURE:
<223> OTHER INFORMATION: Primer

<400> SEQUENCE: 23
tgtaaaacga cggccagtaa agtattacta catagttatc c             41

<210> SEQ ID NO 24
<211> LENGTH: 39
<212> TYPE: DNA
<213> ORGANISM: Artificial Sequence
<220> FEATURE:
<223> OTHER INFORMATION: Primer

<400> SEQUENCE: 24
caggaaacag ctatgaccag ctggggagga gtagagtta                39

<210> SEQ ID NO 25
<211> LENGTH: 38
<212> TYPE: DNA
<213> ORGANISM: Artificial Sequence
<220> FEATURE:
<223> OTHER INFORMATION: Primer

<400> SEQUENCE: 25
tgtaaaacga cggccagttt tcccactaaa ttggatga                 38

<210> SEQ ID NO 26
<211> LENGTH: 32
<212> TYPE: DNA
<213> ORGANISM: Artificial Sequence
<220> FEATURE:
<223> OTHER INFORMATION: Primer

<400> SEQUENCE: 26
caggaaacag ctatgaccct cccgagcccc aa                                    32

<210> SEQ ID NO 27
<211> LENGTH: 39
<212> TYPE: DNA
<213> ORGANISM: Artificial Sequence
<220> FEATURE:
<223> OTHER INFORMATION: Primer

<400> SEQUENCE: 27
tgtaaaacga cggccagtta attagaaatc tcccaagaa                             39

<210> SEQ ID NO 28
<211> LENGTH: 36
<212> TYPE: DNA
<213> ORGANISM: Artificial Sequence
<220> FEATURE:
<223> OTHER INFORMATION: Primer

<400> SEQUENCE: 28
caggaaacag ctatgaccac ggtgctcccc acaaca                                36

<210> SEQ ID NO 29
<211> LENGTH: 38
<212> TYPE: DNA
<213> ORGANISM: Artificial Sequence
<220> FEATURE:
<223> OTHER INFORMATION: Primer

<400> SEQUENCE: 29
tgtaaaacga cggccagttg aggccacctc tcatttgt                              38

<210> SEQ ID NO 30
<211> LENGTH: 41
<212> TYPE: DNA
<213> ORGANISM: Artificial Sequence
<220> FEATURE:
<223> OTHER INFORMATION: Primer

<400> SEQUENCE: 30
caggaaacag ctatgaccat ggtaacttgg gaacatggtt g                          41

<210> SEQ ID NO 31
<211> LENGTH: 37
<212> TYPE: DNA
<213> ORGANISM: Artificial Sequence
<220> FEATURE:
<223> OTHER INFORMATION: Primer

<400> SEQUENCE: 31
tgtaaaacga cggccagttc tttgttagtt tggtata                               37

<210> SEQ ID NO 32
<211> LENGTH: 38
<212> TYPE: DNA
<213> ORGANISM: Artificial Sequence
<220> FEATURE:
<223> OTHER INFORMATION: Primer

```
<400> SEQUENCE: 32
caggaaacag ctatgaccct taaataaagt gttcggta                              38

<210> SEQ ID NO 33
<211> LENGTH: 37
<212> TYPE: DNA
<213> ORGANISM: Artificial Sequence
<220> FEATURE:
<223> OTHER INFORMATION: Primer

<400> SEQUENCE: 33
tgtaaaacga cggccagtta cagccttttta ttatttg                              37

<210> SEQ ID NO 34
<211> LENGTH: 33
<212> TYPE: DNA
<213> ORGANISM: Artificial Sequence
<220> FEATURE:
<223> OTHER INFORMATION: Primer

<400> SEQUENCE: 34
caggaaacag ctatgacccc aaaatgacaa gag                                   33

<210> SEQ ID NO 35
<211> LENGTH: 41
<212> TYPE: DNA
<213> ORGANISM: Artificial Sequence
<220> FEATURE:
<223> OTHER INFORMATION: Primer

<400> SEQUENCE: 35
tgtaaaacga cggccagtag cttacaacga ctgtatttag c                          41

<210> SEQ ID NO 36
<211> LENGTH: 38
<212> TYPE: DNA
<213> ORGANISM: Artificial Sequence
<220> FEATURE:
<223> OTHER INFORMATION: Primer

<400> SEQUENCE: 36
caggaaacag ctatgaccac ccaggctagt tttgattg                              38

<210> SEQ ID NO 37
<211> LENGTH: 37
<212> TYPE: DNA
<213> ORGANISM: Artificial Sequence
<220> FEATURE:
<223> OTHER INFORMATION: Primer

<400> SEQUENCE: 37
tgtaaaacga cggccagttt gcgtatcctt tggaaag                               37

<210> SEQ ID NO 38
<211> LENGTH: 33
<212> TYPE: DNA
<213> ORGANISM: Artificial Sequence
<220> FEATURE:
<223> OTHER INFORMATION: Primer

<400> SEQUENCE: 38
caggaaacag ctatgacctg ccectagcat cca                                   33

<210> SEQ ID NO 39
<211> LENGTH: 37
```

```
<212> TYPE: DNA
<213> ORGANISM: Artificial Sequence
<220> FEATURE:
<223> OTHER INFORMATION: Primer

<400> SEQUENCE: 39
tgtaaaacga cggccagtct ggcttcccag gatgata                    37

<210> SEQ ID NO 40
<211> LENGTH: 43
<212> TYPE: DNA
<213> ORGANISM: Artificial Sequence
<220> FEATURE:
<223> OTHER INFORMATION: Primer

<400> SEQUENCE: 40
caggaaacag ctatgaccgg gaaattactt ttctgggttt acc             43

<210> SEQ ID NO 41
<211> LENGTH: 40
<212> TYPE: DNA
<213> ORGANISM: Artificial Sequence
<220> FEATURE:
<223> OTHER INFORMATION: Primer

<400> SEQUENCE: 41
tgtaaaacga cggccagttt tgtctaatat gaacagaagg                 40

<210> SEQ ID NO 42
<211> LENGTH: 38
<212> TYPE: DNA
<213> ORGANISM: Artificial Sequence
<220> FEATURE:
<223> OTHER INFORMATION: Primer

<400> SEQUENCE: 42
caggaaacag ctatgaccaa gttaaggaaa atggtctg                   38
```

3'-PHOSPHOADENOSINE-5'-PHOSPHOSULFATE SYNTHETASE 1 (PAPSS1) SEQUENCE VARIANTS

CROSS-REFERENCE TO RELATED APPLICATIONS

This application is a divisional of U.S. Ser. No. 10/294,229, filed Nov. 14, 2002, now U.S. Pat. No. 7,067,311 which claims priority from U.S. Provisional Application Ser. No. 60/332,690, filed Nov. 14, 2001.

STATEMENT AS TO FEDERALLY SPONSORED RESEARCH

Funding for the work described herein was provided in part by the federal government under grant nos. R01 GM28157, R01 GM35720, and UO1 GM61388. The federal government may have certain rights in the invention.

TECHNICAL FIELD

The invention relates to PAPSS1 nucleic acid and amino acid sequence variants.

BACKGROUND

Sulfate conjugation is an important pathway in the biotransformation of many neurotransmitters, hormones, drugs and other xenobiotics, and is catalyzed by cytosolic sulfotransferase enzymes designated "SULT." SULT enzymes are encoded by a gene superfamily, which, in mammals, is divided into two families, SULT1 or phenol SULTs and SULT2 or hydroxysteroid SULTs. The SULT1 and SULT2 families share at least 45% amino acid sequence identity, while members of subfamilies within each family share at least 60% amino acid sequence identity. SULT1 subfamilies include the phenol (1A), thyroid hormone (1B), hydroxyarylamine (1C), and estrogen (1E) subfamilies. SULT2 subfamilies include two hydroxysteroid SULTs, 2A1 and 2B1.

Sulfotransferases use 3'-phosphoadenosine 5'-phosphosulfate (PAPS) as a sulfate donor during sulfate conjugation reactions. PAPS is synthesized from ATP and inorganic sulfate by PAPS synthetase (PAPSS). Two PAPSS genes, PAPSS1 and PAPSS2, have been identified in humans. Xu et al., *Biochem. Biophys. Res. Commun.* (2000) 268(2):437-444. The PAPSS1 cDNA is approximately 2.7 kb in length and was mapped to human chromosome band 4q24 by fluorescence in situ hybridization (FISH) analysis. The PAPSS2 cDNA is approximately 4.2 kb in length and was mapped to 10q22-23 by FISH.

SUMMARY

The invention is based on the discovery of sequence variants that occur in both coding and non-coding regions of PAPSS1 nucleic acids. Certain PAPSS1 nucleotide sequence variants encode PAPSS1 enzymes that are associated with individual differences in enzymatic activity. Other PAPSS1 sequence variants in non-coding regions of the PAPSS1 nucleic acid may alter regulation of transcription and/or splicing of the PAPSS1 nucleic acid. Discovery of these sequence variants allows individual differences in the sulfate conjugation of drugs and other xenobiotics in humans to be assessed such that particular treatment regimens can be tailored to an individual based on the presence or absence of one or more sequence variants. Identification of PAPSS1 sequence variants also allows predisposition to joint diseases, hormone dependent diseases, or cancer to be assessed in individuals.

In one aspect, the invention features an isolated nucleic acid molecule containing a PAPSS1 nucleic acid sequence, wherein the nucleic acid molecule is at least ten nucleotides in length, and wherein the PAPSS1 nucleic acid sequence comprises a nucleotide sequence variant. The nucleotide sequence variant can be at a position selected from the group consisting of: a) position 675, 997, 1260, or 1591 relative to the adenine of the PAPSS2 translation initiation codon within SEQ ID NO:13; b) position 107 relative to the guanine in the splice donor site of intron 1 within SEQ ID NO:1; c) position −34 relative to the guanine in the splice acceptor site of intron 1 within SEQ ID NO:2; d) position 55 relative to the guanine in the splice donor site of intron 2 within SEQ ID NO:2; e) position 36 relative to the guanine in the splice donor site of intron 3 within SEQ ID NO:3; f) position 18 or 86 relative to the guanine in the splice donor site of intron 4 within SEQ ID NO:4; g) position 143 relative to the guanine in the splice donor site of intron 5 within SEQ ID NO:5; h) position −14 relative to the guanine in the splice acceptor site of intron 8 within SEQ ID NO:9; i) position 12 or 125 relative to the guanine in the splice donor site of intron 10 within SEQ ID NO:10; and j) position −32 or −7 relative to the guanine in the splice acceptor site of intron 10 within SEQ ID NO:11.

The nucleotide sequence variant can be a nucleotide substitution or a nucleotide insertion. The nucleotide sequence variant can be a thymine substitution for cytosine at position 997 relative to the adenine of the PAPSS1 translation initiation codon or a cytosine substitution for guanine at position 1591 relative to the adenine of the PAPSS1 translation initiation codon. The nucleotide sequence variant can be a cytosine substitution for thymine at position 675 relative to the adenine of the PAPSS1 translation initiation codon or a guanine substitution for adenine at position 1260 relative to the adenine of the PAPSS1 translation initiation codon. The nucleotide sequence variant at position 107 relative to the guanine in the splice donor site of intron 1 can be a guanine substitution for cytosine. The nucleotide sequence variant at position −34 relative to the guanine in the splice acceptor site of intron 1 can be an adenine substitution for guanine. The nucleotide sequence variant at position 55 relative to the guanine in the splice donor site of intron 2 can be a thymine substitution for cytosine.

The nucleotide sequence variant at position 36 relative to the guanine in the splice donor site of intron 3 can be a guanine substitution for adenine. The nucleotide sequence variant at position 18 or 86 relative to the guanine in the splice donor site of intron 4 can be a thymine substitution for cytosine at position 18 or an insertion of the sequence 5'-AGTGTTAGA-3' at position 86. The nucleotide sequence variant at position 143 relative to the guanine in the splice donor site of intron 5 can be a cytosine substitution for guanine. The nucleotide sequence variant at position −14 relative to the guanine in the splice acceptor site of intron 8 can be a cytosine substitution for guanine. The nucleotide sequence variant at position 12 or 125 relative to the guanine in the splice donor site of intron 10 can be a thymine substitution for guanine at position 12 or a guanine substitution for adenine at position 125. The nucleotide sequence variant at position −32 or −7 relative to the guanine in the splice acceptor site of intron 10 can be a guanine substitution for cytosine at position −32, a guanine substitution for adenine at position −7.

The PAPSS1 nucleic acid sequence can contain at least two nucleotide sequence variants (e.g., one or more variants at positions 19, 36, 963, 997, and 1260 relative to the adenine of the PAPSS1 translation initiation codon, a variant at position 107 relative to the guanine in the splice donor site of intron 1, a variant at position −34 relative to the guanine in the splice acceptor site of intron 1, a variant at position 36 relative to the guanine in the splice donor site of intron 3, or a variant at position −32 relative to the guanine in the splice acceptor site of intron 10). The at least two sequence variants can be at position 19 relative to the adenine of the PAPSS1 translation initiation codon and position −34 relative to the guanine in the splice acceptor site of intron 1, or at position 36 relative to the adenine of the PAPSS1 translation initiation codon and position 107 relative to the guanine in the splice donor site of intron 1. The at least two sequence variants can be at position 107 relative to the guanine in the splice donor site of intron 1 and position 963 relative to the adenine of the PAPSS1 translation initiation codon, or at position 36 relative to the adenine of the PAPSS1 translation initiation codon, position 107 relative to the guanine in the splice donor site of intron 1, and position 36 relative to the guanine in the splice donor site of intron 3. The at least two sequence variants can be at position 963 relative to the adenine of the PAPSS1 translation initiation codon, position −34 relative to the guanine in the splice acceptor site of intron 1, and position −32 relative to the guanine in the splice acceptor site of intron 10. The at least two sequence variants can be at positions 19 and 1260 relative to the adenine of the PAPSS1 translation initiation codon, and position −34 relative to the guanine in the splice acceptor site of intron 1, or at positions 19 and 997 relative to the adenine of the PAPSS1 translation initiation codon and position −34 relative to the guanine in the splice acceptor site of intron 1.

In another aspect, the invention features an isolated nucleic acid encoding a PAPSS1 polypeptide, wherein the polypeptide contains a PAPSS1 amino acid sequence variant relative to the amino acid sequence of SEQ ID NO:14. The amino acid sequence variant can be at a residue selected from the group consisting of 333 and 531 (e.g., a cysteine at residue 333 or a glutamine at residue 531).

In another aspect, the invention features an isolated PAPSS1 polypeptide, wherein the polypeptide contains a PAPSS1 amino acid sequence variant relative to the amino acid sequence of SEQ ID NO:14. The amino acid sequence variant can be at a residue selected from the group consisting of 333 and 531 (e.g., a cysteine at residue 333 or a glutamine at residue 531). Activity of the polypeptide can be altered relative to a wild type PAPSS1 polypeptide.

The invention also features an isolated nucleic acid molecule containing a PAPSS1 nucleic acid sequence, wherein the nucleic acid molecule is at least ten nucleotides in length, wherein the PAPSS1 nucleic acid sequence has at least 99% sequence identity to a region of SEQ ID NO:8 or SEQ ID NO:11. Nucleotide 997 relative to the adenine of the PAPSS1 translation initiation codon can be a thymine, or nucleotide 1591 relative to the adenine of the PAPSS1 translation initiation codon can be a cytosine. The region can be selected from the group consisting of: a) nucleotides 925 to 1000 of SEQ ID NO:8 relative to the adenine of the PAPSS1 translation initiation codon; and b) nucleotides 1550 to 1650 of SEQ ID NO:11 relative to the adenine of the PAPSS1 translation initiation codon.

In yet another aspect, the invention features an article of manufacture including a substrate, wherein the substrate includes a population of isolated PAPSS1 nucleic acid molecules, and wherein the nucleic acid molecules include a PAPSS1 nucleotide sequence variant. The substrate can include a plurality of discrete regions, wherein each region includes a different population of isolated PAPSS1 nucleic acid molecules, and wherein each population of molecules includes a different PAPSS1 nucleotide sequence variant.

The invention also features a method for determining if a mammal is predisposed to a joint disease. The method includes obtaining a biological sample from a mammal, and detecting the presence or absence of a PAPSS1 nucleotide sequence variant in the sample, wherein predisposition to a joint disease is determined based on the presence or absence of a variant. The method can further include detecting the presence or absence of a plurality of PAPSS1 nucleotide sequence variants in the sample to obtain a variant profile of the mammal, and wherein predisposition to a joint disease is determined based on the variant profile.

The invention also features a method for determining if a mammal is predisposed to cancer. The method includes obtaining a biological sample from a mammal, and detecting the presence or absence of a PAPSS1 nucleotide sequence variant in the sample, wherein predisposition to cancer is determined based on the presence or absence of a variant. The method can also include detecting the presence or absence of a plurality of PAPSS1 nucleotide sequence variants in the sample to obtain a variant profile of the mammal, and wherein predisposition to cancer is determined based on the variant profile. The cancer can be a chemically induced cancer.

In another aspect, the invention features a method for assisting a medical or research professional. The method includes obtaining a biological sample from a mammal, and detecting the presence or absence of a plurality of PAPSS1 nucleotide sequence variants in the sample to obtain a variant profile of the mammal. The method can further include communicating the profile to the medical or research professional.

The invention also features an isolated nucleic acid molecule including a PAPSS1 nucleic acid sequence, wherein the nucleic acid molecule is at least ten nucleotides in length, and wherein the PAPSS1 nucleic acid sequence includes at least two nucleotide sequence variants. The variants can be within any combination of coding sequences, intron sequences, 5' untranslated sequences, or 3' untranslated sequences. For example, the variants can be selected from the group consisting of a variant at positions 19, 36, 963, 997, 1260, and 1591 relative to the adenine of the PAPSS1 translation initiation codon, a variant at position 107 relative to the guanine in the splice donor site of intron 1, a variant at position −34 relative to the guanine in the splice acceptor site of intron 1, a variant at position 36 relative to the guanine in the splice donor site of intron 3, and a variant at position −32 relative to the guanine in the splice acceptor site of intron 10. The variants can be at position 19 relative to the adenine of the PAPSS1 translation initiation codon and position −34 relative to the guanine in the splice acceptor site of intron 1. The variants can be at position 36 relative to the adenine of the PAPSS1 translation initiation codon and position 107 relative to the guanine in the splice donor site of intron 1. The variants can be at position 107 relative to the guanine in the splice donor site of intron 1 and 963 relative to the adenine of the PAPSS1 translation initiation codon. Further, the variants can be at position 36 relative to the adenine of the PAPSS1 translation initiation codon, position 107 relative to the guanine in the splice donor site of intron 1, and position 36 relative to the guanine in the splice donor site of intron 3. The variants can be at positions 19 and 963 relative to the adenine of the PAPSS1 translation initiation codon, position −34 relative to the guanine in the splice acceptor site of intron 1, and position −32 relative to the guanine in the splice acceptor site of intron 10.

The variants can also be at positions 19 and 1260 relative to the adenine of the PAPSS1 translation initiation codon, and position −34 relative to the guanine in the splice acceptor site of intron 1. The variants can be at positions 19 and 997 relative to the adenine of the PAPSS1 translation initiation codon and position −34 relative to the guanine in the splice acceptor site of intron 1.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 1 is the nucleotide sequence of the reference PAPSS1 (SEQ ID NOS:1-12). Single nucleotide polymorphisms (SNPs) are circled, exons are in uppercase, introns are in lowercase, coding regions are in boldface, and primer sequences are underlined.

FIG. 2A is a cDNA sequence (SEQ ID NO:13) containing the ORF of the reference PAPSS1 (nucleotides 55-1929). FIG. 2B is the amino acid sequence (SEQ ID NO:14) of the reference PAPSS1.

DETAILED DESCRIPTION

Figure 3:
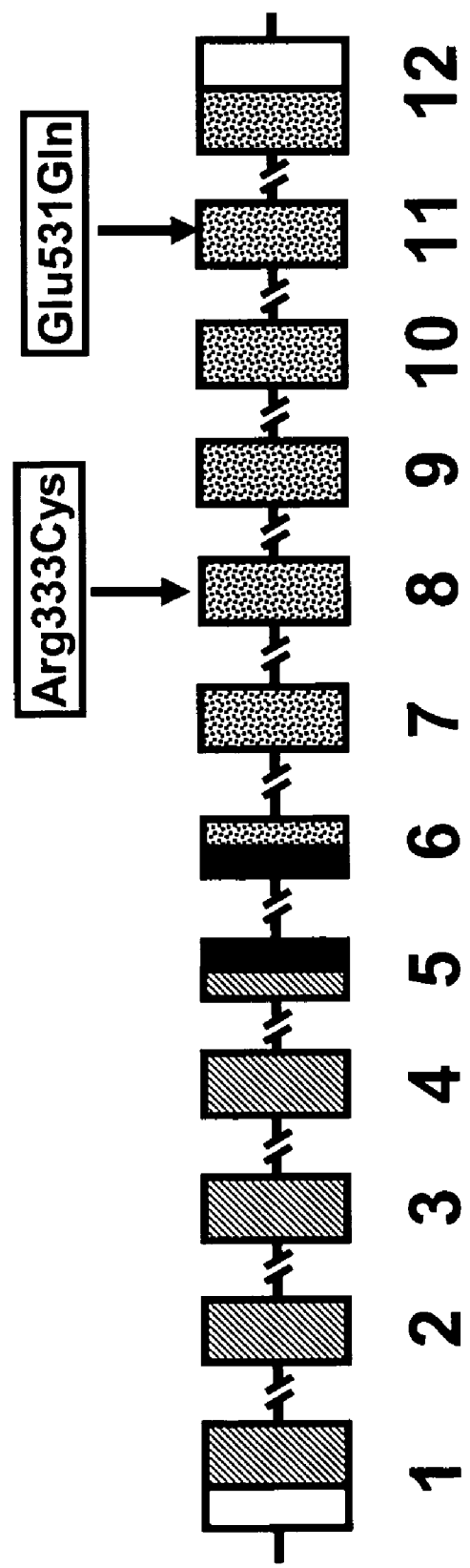
FIG. 3 is a schematic of the location of the non-synonymous polymorphisms within the PAPSS 1 sequence.

The invention features PAPSS1 nucleotide and amino acid sequence variants. PAPSS1 is one of two enzymes that synthesize PAPS, the high energy sulfate donor used in the sulfate conjugation of drugs, hormones (e.g., estrogen), neurotransmitters (e.g., dopamine), and other endogenous compounds. Sulfation typically detoxifies compounds as the resulting ionized, organic sulfates are more readily excreted than the unsulfated compounds. Furthermore, functional groups that may interact with biological macromolecules such as nucleic acids or proteins can be masked by the sulfate moiety. Sulfation of certain compounds, however, such as the hydroxy metabolite of 2-acetylaminofluorene (AAF), produces sulfate conjugates that are chemically unstable and that can degrade to form reactive, electrophilic species. In particular, sulfation of the hydroxy metabolite of AAF produces a reactive N—O-sulfate ester, which can rearrange and fragment into a reactive electrophilic species that can bind to nucleic acids and proteins. Thus, detecting PAPSS nucleic acid and amino acid sequence variants can facilitate the prediction of therapeutic efficacy and toxicity of drugs on an individual basis, as well as the ability to biotransform certain hormones and neurotransmitters. Furthermore, inactivation of the PAPSS gene results in severe, early degenerative arthritis. Thus, detecting PAPSS nucleic acid and amino acid variants can be used to determine predisposition to joint diseases such as osteoarthritis.

Nucleic Acid Molecules

The invention features isolated nucleic acids that include a PAPSS1 nucleic acid sequence. The PAPSS1 nucleic acid sequence includes a nucleotide sequence variant and nucleotides flanking the sequence variant. As used herein, "isolated nucleic acid" refers to a nucleic acid that is separated from other nucleic acid molecules that are present in a mammalian genome, including nucleic acids that normally flank one or both sides of the nucleic acid in a mammalian genome (e.g., nucleic acids that encode non-PAPSS1 proteins). The term "isolated" as used herein with respect to nucleic acids also includes any non-naturally-occurring nucleic acid sequence since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

Nucleic acids of the invention are at least about 8 nucleotides in length. For example, the nucleic acid can be about 8, 9, 10-20 (e.g., 11, 12, 13, 14, 15, 16, 17, 18, 19, or 20 nucleotides in length), 20-50, 50-100 or greater than 100 nucleotides in length (e.g., greater than 150, 200, 250, 300, 350, 400, 450, 500, 750, or 1000 nucleotides in length). Nucleic acids of the invention can be in a sense or antisense orientation, can be complementary to the PAPSS1 reference sequence, and can be DNA, RNA, or nucleic acid analogs. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine or 5-bromo-2'-doxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, Summerton and Weller, *Antisense Nucleic Acid Drug Dev.* (1997) 7(3):187-195; and Hyrup et al. (1996) *Bioorgan. Med. Chem.* 4(1):5-23. In addition, the deoxyphosphate backbone can be replaced with, for example, a phosphorothioate or phosphorodithioate backbone, a phosphoramidite, or an alkyl phosphotriester backbone.

As used herein, "nucleotide sequence variant" refers to any alteration in a PAPSS1 reference sequence, and includes variations that occur in coding and non-coding regions, including exons, introns, and untranslated sequences. Nucleotides are referred to herein by the standard one-letter designation (A, C, G, or T). Variations include single nucleotide substitutions, deletions of one or more nucleotides, and insertions of one or more nucleotides. The reference PAPSS1 nucleic acid sequence is provided in FIG. 1 (SEQ ID NOS:1-12) and in GenBank (Accession Nos. AF097710-AF097721). The reference PAPSS1 cDNA including the PAPSS1 ORF is provided in FIG. 2A (SEQ ID NO:13) and the corresponding reference PAPSS1 amino acid sequence is provided in FIG. 2B (SEQ ID NO:14). The mRNA and amino acid reference sequences also are found in GenBank (Accession No. AF105227). The nucleic acid and amino acid reference sequences also are referred to herein as "wild type."

As used herein, "untranslated sequence" includes 5' and 3' flanking regions that are outside of the messenger RNA (mRNA) as well as 5' and 3' untranslated regions (5'-UTR or 3'-UTR) that are part of the mRNA, but are not translated. Positions of nucleotide sequence variants in 5' untranslated sequences are designated as "−X" relative to the "A" in the translation initiation codon; positions of nucleotide sequence variants in the coding sequence and 3' untranslated sequence are designated as "+X" or "X" relative to the "A" in the translation initiation codon. Nucleotide sequence variants that occur in introns are designated as "+X" or "X" relative to the "G" in the splice donor site (GT) or as "−X" relative to the "G" in the splice acceptor site (AG).

In some embodiments, a PAPSS1 nucleotide sequence variant encodes a PAPSS1 polypeptide having an altered amino acid sequence. The term "polypeptide" refers to a chain of at least four amino acid residues (e.g., 4-8, 9-12, 13-15, 16-18, 19-21, 22-100, 100-150, 150-200, 200-300 residues, or a full-length PAPSS1 polypeptide). PAPSS1 polypeptides may or may not have PAPSS catalytic activity, or may have altered activity relative to the reference PAPSS1 polypeptide. Polypeptides that do not have activity or have altered activity are useful for diagnostic purposes (e.g., for producing antibodies having specific binding affinity for variant PAPSS polypeptides).

Corresponding PAPSS1 polypeptides, irrespective of length, that differ in amino acid sequence are herein referred to as allozymes. For example, a PAPSS1 nucleic acid sequence that includes a thymine at nucleotide 997 encodes a PAPSS1 polypeptide having a cysteine at amino acid residue 333. This polypeptide (Arg333Cys) would be considered an allozyme with respect to the reference PAPSS1 polypeptide that contains an arginine at amino acid residue 333. Additional non-limiting examples of PAPSS1 sequence variants that alter amino acid sequence include variants at nucleotides 810, 1064, and 1591. For example, a PAPSS1 nucleic acid molecule can include a cytosine at nucleotide 810 and encode a PAPSS1 polypeptide having a phenylalanine at amino acid residue 270 in place of a leucine residue (Leu270Phe); a guanine at nucleotide 1064 and encode a PAPSS1 polypeptide having an arginine at amino acid 355 in place of a glutamine (Gln355Arg); or a cytosine at nucleotide 1591 and encode a PAPSS1 polypeptide having a glutamine at amino acid 531 in place of a glutamic acid (Glu531Gln).

PAPSS1 allozymes as described above are encoded by a series of PAPSS alleles. These alleles represent nucleic acid sequences containing sequence variants, typically multiple sequence variants, within coding and non-coding sequences. Representative examples of single nucleotide variants are described above. Table 2 sets out a series of PAPSS1 alleles that encode PAPSS1. Some alleles are commonly observed, i.e., have an allele frequencies >1%, such as alleles encoding Arg333Cys. The relatively large number of alleles and allozymes for PAPSS1 indicates the potential complexity of PAPSS pharmacogenetics. Such complexity emphasizes the need for determining single nucleotide variants, (i.e., single nucleotide polymorphisms, SNPs) as well as complete PAPSS1 haplotypes (i.e., the set of alleles on one chromosome or a part of a chromosome) of patients. See Table 4 for haplotypes of PAPSS1.

Certain PAPSS1 nucleotide sequence variants do not alter the amino acid sequence. Such variants, however, could alter regulation of transcription as well as mRNA stability. PAPSS1 variants can occur in intron sequences, for example, within introns 1, 2, 3, 4, 5, 6, 7, 8, 9, 10, or 11. In particular, the nucleotide sequence variant can include a guanine substitution at nucleotide 107, or an adenine substitution at nucleotide −34 of intron 1. Intron 2 variants can include a thymine substitution at nucleotide 55. Intron 3 variants include a guanine substitution at nucleotide 36. Intron 4 sequence variants can include a thymine substitution at nucleotide 18, or a 9 bp insertion (5'-AGTGTTAGA-3') at nucleotide 86. The nucleotide sequence variant can include a cytosine substitution at nucleotide 143 of intron 5. Intron 8 sequence variants can include a cytosine substitution at nucleotide −14. Intron 10 sequence variants can include a thymine substitution at nucleotide 12, a guanine substitution at nucleotide 125, a guanine substitution at nucleotide −32, or a guanine substitution at nucleotide −7.

PAPSS1 nucleotide sequence variants that do not change the amino acid sequence also can be within an exon or in 5' or 3' untranslated sequences. Exon 1 sequence variants can, for example, include a thymine substitution at nucleotide 19, or an adenine substitution at nucleotide 36. Exon 6 sequence variants can include a cytosine substitution at nucleotide 675. Sequence variants can also include a thymine substitution at nucleotide 963 of exon 8. Nucleotide sequence variants the 5' untranslated region of PAPSS1 can include a thymine substitution at −44. The 3' UTR can include an adenine substitution at 1945.

In some embodiments, nucleic acid molecules of the invention can have at least 97% (e.g., 97.5%, 98%, 98.5%, 99.0%, 99.5%, 99.6%, 99.7%, 99.8%, 99.9%, or 100%) sequence identity with a region of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, or SEQ ID NO:12 that includes one or more variants described herein. The region of SEQ ID NO:1, 2, 3, 4, 5, 6, 7, 8, 9, 10, 11, or 12 is at least ten nucleotides in length (e.g., ten, 15, 20, 50, 60, 70, 75, 100, 150 or more nucleotides in length). For example, a nucleic acid molecule can have at least 99% identity with a region of SEQ ID NO: 1 containing nucleotides −100 to −1 or 1 to 75 relative to the adenine of the PAPSS2 translation initiation codon, or a region of SEQ ID NO:1 containing nucleotides 50 to 150 relative to the guanine in the splice donor site of intron 1, where the nucleotide sequence of SEQ ID NO:1 includes one or more of the variants described herein.

For example, the nucleotide sequence of SEQ ID NO:1 can have a thymine at nucleotide −44 relative to the adenine of the PAPSS2 translation initiation codon, a thymine at nucleotide 19 relative to the adenine of the PAPSS2 translation initiation codon, an adenine at nucleotide 36 relative to the adenine of the PAPSS2 translation initiation codon, or a guanine at nucleotide 107 relative to the guanine in the splice donor site of intron 1, and combinations thereof In another embodiment, a nucleic acid molecule can have at least 99% identity with a region of SEQ ID NO:2 containing nucleotides −75 to −1 relative to the guanine in the splice acceptor site of intron 1, or nucleotides 1 to 100 relative to the guanine in the splice donor site of intron 2, where the nucleotide sequence of SEQ ID NO:2 includes one or more of the variants described herein. For example, the nucleotide sequence of SEQ ID NO:2 can have an adenine thymine at nucleotide −34 relative to the guanine of the splice acceptor site of intron 1, or an adenine at nucleotide 55 relative to the guanine in the splice donor site of intron 2, and combinations thereof.

In another embodiment, a nucleic acid molecule can have at least 99% identity with a region of SEQ ID NO:3 containing nucleotides 1 to 75 relative to the guanine in the splice donor site of intron 3, where the nucleotide sequence of SEQ ID NO:3 includes one or more of the variants described herein. For example, the nucleotide sequence of SEQ ID NO:3 can have a guanine at nucleotide 36 relative to the guanine in the splice donor site of intron 3. A nucleic acid molecule also can have at least 98% identity with a region of SEQ ID NO:4 containing nucleotides 1 to 75 or 25 to 125 relative to the guanine in the splice donor site of intron 4, where the nucleotide sequence of SEQ ID NO:4 includes one or more of the variants described herein. For example, the nucleotide sequence of SEQ ID NO:4 can have a thymine at nucleotide 18 or an insertion of the sequence 5'-AGTGTTAGA-3' at nucleotide 86 relative to the guanine in the splice donor site of intron 4, and a combination thereof. In another embodiment, a nucleic acid molecule can have at least 99% identity with a region of SEQ ID NO:5 containing nucleotides 100 to 200 relative to the guanine in the splice donor site of intron 5, where the nucleotide sequence of SEQ ID NO:5 includes one or more of the variants described herein. For example, the nucleotide sequence of SEQ ID NO:5 can have a cytosine at nucleotide 144 relative to the guanine in the splice donor site of intron 5. In yet another embodiment, a nucleic acid molecule can have at least 99% identity with a region of SEQ ID NO:6 containing nucleotides 670 to 750 relative to the adenine in the PAPSS1 translation initiation site, where the nucleotide sequence of SEQ ID NO:6 includes one or more of the variants described herein. For example, the nucleotide sequence of SEQ ID NO:6 can have a cytosine at nucleotide 675 relative to the adenine in the PAPSS1 translation initiation site.

In still another embodiment, a nucleic acid molecule can have at least 99% identity with a region of SEQ ID NO:8 containing nucleotides 925 to 1000 or 950 to 1050 relative to the adenine in the PAPSS1 translation initiation site, where the nucleotide sequence of SEQ ID NO:8 includes one or more of the variants described herein. For example, the nucleotide sequence of SEQ ID NO:8 can have a thymine at nucleotide 963 relative to the adenine in the PAPSS1 translation initiation site, a thymine at nucleotide 997 relative to the adenine in the PAPSS1 translation initiation site, and a combination thereof. In another embodiment, a nucleic acid molecule can have at least 99% identity with a region of SEQ ID NO:9 containing nucleotides −75 to −1 relative to the guanine in the splice acceptor of intron 8, where the nucleotide sequence of SEQ ID NO:9 includes one or more of the variants described herein. For example, the nucleotide sequence of SEQ ID NO:9 can have a cytosine at nucleotide −14 relative to the guanine in the splice acceptor site of intron 8. In another embodiment, a nucleic acid molecule can have at least 99% identity with a region of SEQ ID NO:10 containing nucleotides 1238 to 1300 relative to the adenine in the PAPSS1 translation initiation site, or nucleotides 1 to 75 or 80 to 175 relative to the guanine in the splice donor site of intron 10, where the nucleotide sequence of SEQ ID NO:10 includes one or more of the variants described herein. For example, the nucleotide sequence of SEQ ID NO:10 can have a guanine at nucleotide 1260 relative to the adenine of the PAPSS2 translation initiation codon, a thymine at nucleotide 12 or a guanine at nucleotide 125 relative to the guanine in the splice donor site of intron 10, and combinations thereof.

In yet another embodiment, a nucleic acid molecule can have at least 99% identity with a region of SEQ ID NO:11 containing nucleotides −75 to −1 relative to the guanine in the splice acceptor site of intron 10, or nucleotides 1550 to 1650 relative to the adenine of the PAPSS2 translation initiation codon, where the nucleotide sequence of SEQ ID NO:11 includes one or more of the variants described herein. For example, the nucleotide sequence of SEQ ID NO:11 can have a guanine at nucleotide −32 or a guanine at nucleotide −7 relative to the guanine in the splice acceptor site of intron 10, or a cytosine at nucleotide 1591 relative to the adenine of the PAPSS2 translation initiation codon, and combinations thereof. In another embodiment, a nucleic acid molecule can have at least 99% identity with a region of SEQ ID NO:12 containing nucleotides 1900 to 2000 relative to the adenine of the PAPSS2 translation initiation codon, where the nucleotide sequence of SEQ ID NO:12 includes one or more of the variants described herein. For example, the nucleotide sequence of SEQ ID NO:12 can have an adenine at nucleotide 1945 relative to the adenine of the PAPSS2 translation initiation codon.

Percent sequence identity is calculated by determining the number of matched positions in aligned nucleic acid sequences, dividing the number of matched positions by the total number of aligned nucleotides, and multiplying by 100. A matched position refers to a position in which identical nucleotides occur at the same position in aligned nucleic acid sequences. Percent sequence identity also can be determined for any amino acid sequence. To determine percent sequence identity, a target nucleic acid or amino acid sequence is compared to the identified nucleic acid or amino acid sequence using the BLAST 2 Sequences (Bl2seq) program from the stand-alone version of BLASTZ containing BLASTN version 2.0.14 and BLASTP version 2.0.14. This stand-alone version of BLASTZ can be obtained from Fish & Richardson's web site (www.fr.com/blast) or the U.S. government's National Center for Biotechnology Information web site (www.ncbi.nlm.nih.gov). Instructions explaining how to use the Bl2seq program can be found in the readme file accompanying BLASTZ.

Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to −1; -r is set to 2; and all other options are left at their default setting. The following command will generate an output file containing a comparison between two sequences: C:\B12seq -i c:\seq1.txt -j c:\seq2.txt -p blastn -o c:\output.txt -q -1 -r 2. If the target sequence shares homology with any portion of the identified sequence, then the designated output file will present those regions of homology as aligned sequences. If the target sequence does not share homology with any portion of the identified sequence, then the designated output file will not present aligned sequences.

Once aligned, a length is determined by counting the number of consecutive nucleotides from the target sequence presented in alignment with sequence from the identified sequence starting with any matched position and ending with any other matched position. A matched position is any position where an identical nucleotide is presented in both the target and identified sequence. Gaps presented in the target sequence are not counted since gaps are not nucleotides. Likewise, gaps presented in the identified sequence are not counted since target sequence nucleotides are counted, not nucleotides from the identified sequence.

The percent identity over a particular length is determined by counting the number of matched positions over that length and dividing that number by the length followed by multiplying the resulting value by 100. For example, if (1) a 1000 nucleotide target sequence is compared to the sequence set forth in SEQ ID NO:1, (2) the B12seq program presents 969 nucleotides from the target sequence aligned with a region of the sequence set forth in SEQ ID NO:1 where the first and last nucleotides of that 969 nucleotide region are matches, and (3) the number of matches over those 969 aligned nucleotides is 900, then the 1000 nucleotide target sequence contains a length of 969 and a percent identity over that length of 93 (i.e., 900 969×100=93).

It will be appreciated that different regions within a single nucleic acid target sequence that aligns with an identified sequence can each have their own percent identity. It is noted that the percent identity value is rounded to the nearest tenth. For example, 78.11, 78.12, 78.13, and 78.14 are rounded down to 78.1, while 78.15, 78.16, 78.17, 78.18, and 78.19 are rounded up to 78.2. It also is noted that the length value will always be an integer.

Isolated nucleic acid molecules of the invention can be produced by standard techniques, including, without limitation, common molecular cloning and chemical nucleic acid synthesis techniques. For example, polymerase chain reaction (PCR) techniques can be used to obtain an isolated nucleic acid containing a PAPSS1 nucleotide sequence variant. PCR refers to a procedure or technique in which target nucleic acids are enzymatically amplified. Sequence information from the ends of the region of interest or beyond typically is employed to design oligonucleotide primers that are identical in sequence to opposite strands of the template to be amplified. PCR can be used to amplify specific sequences from DNA as well as RNA, including sequences from total genomic DNA or total cellular RNA. Primers are typically 14 to 40 nucleotides in length, but can range from 10 nucleotides to hundreds of nucleotides in length. General PCR techniques are described, for example in *PCR Primer: A Laboratory Manual*, ed. by Dieffenbach and Dveksler, Cold Spring Harbor Laboratory Press, 1995. When using RNA as a source of template, reverse transcriptase can be used to synthesize complementary DNA (cDNA) strands. Ligase chain reaction, strand displacement amplification, self-sustained sequence replication, or nucleic acid sequence-based amplification also can be used to obtain isolated nucleic acids. See, for example, Lewis *Genetic Engineering News*, 12(9):1 (1992); Guatelli et al., *Proc. Natl. Acad. Sci. USA*, 87:1874-1878 (1990); and Weiss, *Science*, 254:1292 (1991).

Isolated nucleic acids of the invention also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector.

Isolated nucleic acids of the invention also can be obtained by mutagenesis. For example, the reference sequences depicted in FIGS. 1 or 2A can be mutated using standard techniques including oligonucleotide-directed mutagenesis and site-directed mutagenesis through PCR. See, *Short Protocols in Molecular Biology*, Chapter 8, Green Publishing Associates and John Wiley & Sons, edited by Ausubel et al., 1992. Examples of positions that can be modified are described above.

PAPSS1 Polypeptides

Isolated PAPSS1 polypeptides of the invention include an amino acid sequence variant relative to the reference PAPSS1 (FIG. 2B, GenBank Accession No. AF105227). The term "isolated" with respect to a PAPSS1 polypeptide refers to a polypeptide that has been separated from cellular components by which it is naturally accompanied. Typically, the polypeptide is isolated when it is at least 60% (e.g., 70%, 80%, 90%, 95%, or 99%), by weight, free from proteins and naturally-occurring organic molecules with which it is naturally associated. In general, an isolated polypeptide will yield a single major band on a non-reducing polyacrylamide gel.

PAPSS1 polypeptides of the invention include variants at one or more of amino acid residues 333 and 531. In particular, a cysteine residue can be substituted at position 333, or a glutamine at position 531.

In some embodiments, activity of PAPSS1 polypeptides is altered relative to the reference PAPSS1. As described herein, certain PAPSS1 allozymes have reduced activity (e.g., Arg333Cys), while other allozymes (e.g., Glu531Gln) have activity that is comparable to the reference PAPSS1. Other allozymes can have increased activity relative to the reference PAPSS1. Activity of PAPSS1 polypeptides can be assessed in vitro. For example, recombinant PAPSS1 polypeptides can be used to generate PAPS from ATP and inorganic sulfate. The activity of PAPSS1 polypeptides can then be indirectly assessed by determining the amount of sulfated 17 β-[$^3$H] estradiol that is produced by a recombinant sulfotransferase (e.g., recombinant SUTL1E1) in the presence of the generated PAPS. See, Xu et al. *Drug. Metab. Dispos.* (2001) 29(2):172-178.

Other biochemical properties of allozymes, such as apparent $K_m$ values, also can be altered relative to the reference PAPSS1. Apparent $K_m$ values can be calculated, for example, by using the method of Wilkinson with a computer program written by Cleland. Wilkinson, *Biochem. J.*, 80:324-332 (1961); and Cleland, *Nature*, 198:463-365 (1963).

Isolated polypeptides of the invention can be obtained, for example, by extraction from a natural source (e.g., liver tissue), chemical synthesis, or by recombinant production in a host cell. To recombinantly produce PAPSS1 polypeptides, a nucleic acid encoding a PAPSS1 nucleotide sequence variant can be ligated into an expression vector and used to transform a prokaryotic (e.g., bacteria) or eukaryotic (e.g., insect, yeast, or mammal) host cell. In general, nucleic acid constructs include a regulatory sequence operably linked to a PAPSS nucleic acid sequence. Regulatory sequences (e.g., promoters, enhancers, polyadenylation signals, or terminators) do not typically encode a gene product, but instead affect the expression of the nucleic acid sequence. In addition, a construct can include a tag sequence designed to facilitate subsequent manipulations of the expressed nucleic acid sequence (e.g., purification, localization). Tag sequences, such as green fluorescent protein (GFP), glutathione S-transferase (GST), six histidine ($His_6$), c-myc, hemagglutinin, or Flag™ tag (Kodak) sequences are typically expressed as a fusion with the expressed nucleic acid sequence. Such tags can be inserted anywhere within the polypeptide including at either the carboxyl or amino termini. The type and combination of regulatory and tag sequences can vary with each particular host, cloning or expression system, and desired outcome. A variety of cloning and expression vectors containing combinations of regulatory and tag sequences are commercially available. Suitable cloning vectors include, without limitation, pUC18, pUC19, and pBR322 and derivatives thereof (New England Biolabs, Beverly, Mass.), and pGEN (Promega, Madison, Wis.). Additionally, representative prokaryotic expression vectors include pBAD (Invitrogen, Carlsbad, Calif.), the pTYB family of vectors (New England Biolabs), and pGEMEX vectors (Promega); representative mammalian expression vectors include pTet-On/pTet-Off(Clontech, Palo Alto, Calif.), pIND, pVAX1, pCR3.1, pcDNA3.1, pcDNA4, or pUni (Invitrogen), and pCI or pSI (Promega); representative insect expression vectors include pBacPAK8 or pBacPAK9 (Clontech), and p2Bac (Invitrogen); and representative yeast expression vectors include MATCHMAKER (Clontech) and pPICZ A, B, and C (Invitrogen).

In bacterial systems, a strain of *Escherichia coli* can be used to express PAPSS1 variant polypeptides. For example, BL-21 cells can be transformed with a pGEX vector containing a PAPSS1 nucleic acid sequence. The transformed bacteria can be grown exponentially and then stimulated with isopropylthiogalactopyranoside (IPTG) prior to harvesting. In general, the PAPSS1-GST fusion proteins produced from the pGEX expression vector are soluble and can be purified easily from lysed cells by adsorption to glutathione-agarose beads followed by elution in the presence of free glutathione. The pGEX vectors are designed to include thrombin or factor Xa protease cleavage sites so that the expressed PAPSS1 polypeptide can be released from the GST moiety.

In eukaryotic host cells, a number of viral-based expression systems can be utilized to express PAPSS1 variant polypeptides. A nucleic acid encoding a polypeptide of the invention can be cloned into, for example, a baculoviral vector such as pBlueBac (Invitrogen) and then used to co-transfect insect cells such as *Spodoptera frugiperda* (Sf9) cells with wild type DNA from *Autographa californica* multinuclear polyhedrosis virus (AcMNPV). Recombinant viruses producing polypeptides of the invention can be identified by standard methodology. Alternatively, a nucleic acid encoding a polypeptide of the invention can be introduced into a SV40, retroviral, or vaccinia based viral vector and used to infect suitable host cells.

Eukaryotic cell lines that stably express PAPSS1 variant polypeptides can be produced using expression vectors with the appropriate control elements and a selectable marker. For example, the eukaryotic expression vector pCR3.1 (Invitrogen, San Diego, Calif.) and p91023(B) (see Wong et al., *Science* (1985) 228:810-815) or modified derivatives thereof are suitable for expression of PAPSS1 variant polypeptides in, for example, Chinese hamster ovary (CHO) cells, COS-1 cells, human embryonic kidney 293 cells, NIH3T3 cells, BHK21 cells, MDCK cells, and human vascular endothelial cells (HUVEC). Following introduction of the expression vector by electroporation, lipofection, calcium phosphate or calcium chloride co-precipitation, DEAE dextran, or other suitable transfection method, stable cell lines are selected, e.g., by antibiotic resistance to G418, kanamycin, or hygromycin. Alternatively, amplified sequences can be ligated into a eukaryotic expression vector such as pcDNA3 (Invitrogen) and then transcribed and translated in vitro using wheat germ extract or rabbit reticulocyte lysate.

PAPSS1 variant polypeptides can be purified by known chromatographic methods including DEAE ion exchange, gel filtration, and hydroxylapatite chromatography. See, for example, Flohe et al., *Biochim Biophys Acta,* (1970) 220: 469-476; and Tilgmann et al., *FEBS* (1990) 264:95-99. PAPSS1 polypeptides can be "engineered" to contain a tag sequence describe herein that allows the polypeptide to be purified (e.g., captured onto an affinity matrix). Immunoaffinity chromatography also can be used to purify PAPSS1 polypeptides.

Non-Human Mammals

The invention features non-human mammals that include PAPSS1 nucleic acids of the invention, as well as progeny and cells of such non-human mammals. Non-human mammals include, for example, rodents such as rats, guinea pigs, and mice, and farm animals such as pigs, sheep, goats, horses, and cattle. Non-human mammals of the invention can express a PAPSS1 variant nucleic acid in addition to an endogenous PAPSS1 (e.g., a transgenic non-human that includes a PAPSS1 nucleic acid randomly integrated into the genome of the non-human mammal). Alternatively, an endogenous PAPSS1 nucleic acid can be replaced with a PAPSS1 variant nucleic acid of the invention by homologous recombination. See, Shastry, *Mol. Cell Biochem.,* (1998) 181(1-2):163-179, for a review of gene targeting technology.

In one embodiment, non-human mammals are produced that lack an endogenous PAPSS1 nucleic acid (i.e., a knockout), and then a PAPSS1 variant nucleic acid of the invention is introduced into the knockout non-human mammal. Nucleic acid constructs used for producing knockout non-human mammals can include a nucleic acid sequence encoding a selectable marker, which is generally used to interrupt the targeted exon site by homologous recombination. Typically, the selectable marker is flanked by sequences homologous to the sequences flanking the desired insertion site. It is not necessary for the flanking sequences to be immediately adjacent to the desired insertion site. Suitable markers for positive drug selection include, for example, the aminoglycoside 3N phosphotransferase gene that imparts resistance to geneticin (G418, an aminoglycoside antibiotic), and other antibiotic resistance markers, such as the hygromycin-B-phosphotransferase gene that imparts hygromycin resistance. Other selection systems include negative-selection markers such as the thymidine kinase (TK) gene from herpes simplex virus. Constructs utilizing both positive and negative drug selection also can be used. For example, a construct can contain the aminoglycoside phosphotransferase gene and the TK gene. In this system, cells are selected that are resistant to G418 and sensitive to gancyclovir.

To create non-human mammals having a particular gene inactivated in all cells, it is necessary to introduce a knockout construct into the germ cells (sperm or eggs, i.e., the "germ line") of the desired species. Genes or other DNA sequences can be introduced into the pronuclei of fertilized eggs by microinjection. Following pronuclear fusion, the developing embryo may carry the introduced gene in all its somatic and germ cells because the zygote is the mitotic progenitor of all cells in the embryo. Since targeted insertion of a knockout construct is a relatively rare event, it is desirable to generate and screen a large number of animals when employing such an approach. Because of this, it can be advantageous to work with the large cell populations and selection criteria that are characteristic of cultured cell systems. However, for production of knockout animals from an initial population of cultured cells, it is necessary that a cultured cell containing the desired knockout construct be capable of generating a whole animal. This is generally accomplished by placing the cell into a developing embryo environment of some sort.

Cells capable of giving rise to at least several differentiated cell types are "pluripotent." Pluripotent cells capable of giving rise to all cell types of an embryo, including germ cells, are hereinafter termed "totipotent" cells. Totipotent murine cell lines (embryonic stem, or "ES" cells) have been isolated by culture of cells derived from very young embryos (blastocysts). Such cells are capable, upon incorporation into an embryo, of differentiating into all cell types, including germ cells, and can be employed to generate animals lacking an endogenous PAPSS1 nucleic acid. That is, cultured ES cells can be transformed with a knockout construct and cells selected in which the PAPSS1 gene is inactivated.

Nucleic acid constructs can be introduced into ES cells, for example, by electroporation or other standard technique. Selected cells can be screened for gene targeting events. For example, the polymerase chain reaction (PCR) can be used to confirm the presence of the transgene.

The ES cells further can be characterized to determine the number of targeting events. For example, genomic DNA can be harvested from ES cells and used for Southern analysis. See, for example, Section 9.37-9.52 of Sambrook et al., *Molecular Cloning, A Laboratory Manual,* second edition, Cold Spring Harbor Press, Plainview; N.Y., 1989.

To generate a knockout animal, ES cells having at least one inactivated PAPSS1 allele are incorporated into a developing embryo. This can be accomplished through injection into the blastocyst cavity of a murine blastocyst-stage embryo, by injection into a morula-stage embryo, by co-culture of ES cells with a morula-stage embryo, or through fusion of the ES cell with an enucleated zygote. The resulting embryo is raised to sexual maturity and bred in order to obtain animals, whose cells (including germ cells) carry the inactivated PAPSS1 allele. If the original ES cell was heterozygous for the inactivated PAPSS1 allele, several of these animals can be bred with each other in order to generate animals homozygous for the inactivated allele.

Alternatively, direct microinjection of DNA into eggs can be used to avoid the manipulations required to turn a cultured cell into an animal. Fertilized eggs are totipotent, i.e., capable of developing into an adult without further substantive manipulation other than implantation into a surrogate mother. To enhance the probability of homologous recombination when eggs are directly injected with knockout constructs, it is useful to incorporate at least about 8 kb of homologous DNA into the targeting construct. In addition, it is also useful to prepare the knockout constructs from isogenic DNA.

Embryos derived from microinjected eggs can be screened for homologous recombination events in several ways. For example, if the PAPSS1 gene is interrupted by a coding region that produces a detectable (e.g., fluorescent) gene product, then the injected eggs are cultured to the blastocyst stage and analyzed for presence of the indicator polypeptide. Embryos with fluorescing cells, for example, are then implanted into a surrogate mother and allowed to develop to term. Alternatively, injected eggs are allowed to develop and DNA from the resulting pups analyzed by PCR or RT-PCR for evidence of homologous recombination.

Nuclear transplantation also can be used to generate non-human mammals of the invention. For example, fetal fibroblasts can be genetically modified such that they contain an inactivated endogenous PAPSS1 gene and express a PAPSS1 nucleic acid of the invention, and then fused with enucleated oocytes. After activation of the oocytes, the eggs are cultured to the blastocyst stage, and implanted into a recipient. See, Cibelli et al., *Science,* (1998) 280:1256-1258. Adult somatic cells, including, for example, cumulus cells and mammary cells, can be used to produce animals such as mice and sheep, respectively. See, for example, Wakayama et al., *Nature,* (1998) 394(6691):369-374; and Wilmut et al., *Nature,* (1997) 385(6619):810-813. Nuclei can be removed from genetically modified adult somatic cells, and transplanted into enucleated oocytes. After activation, the eggs can be cultured to the 2-8 cell stage, or to the blastocyst stage, and implanted into a suitable recipient. Wakayama et al. 1998, supra.

Non-human mammals of the invention such as mice can be used, for example, to screen toxicity of compounds that are substrates for PAPSS1, drugs that alter PAPSS1 activity, or for carcinogenesis. For example, PAPSS1 activity or toxicity can be assessed in a first group of such non-human mammals in the presence of a compound, and compared with PAPSS1 activity or toxicity in a corresponding control group in the absence of the compound. As used herein, suitable compounds include biological macromolecules such as an oligonucleotide (RNA or DNA), or a polypeptide of any length, a chemical compound, a mixture of chemical compounds, or an extract isolated from bacterial, plant, fungal, or animal matter. The concentration of compound to be tested depends on the type of compound and in vitro test data.

Non-human mammals can be exposed to test compounds by any route of administration, including enterally (e.g., orally) and parenterally (e.g., subcutaneously, intravascularly, intramuscularly, or intranasally). Suitable formulations for oral administration can include tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g. magnesium stearate, talc or silica); disintegrants (e.g., potato starch or sodium starch glycolate); or wetting agents (e.g., sodium lauryl sulfate). Tablets can be coated by methods known in the art. Preparations for oral administration can also be formulated to give controlled release of the compound.

Compounds can be prepared for parenteral administration in liquid form (e.g., solutions, solvents, suspensions, and emulsions) including sterile aqueous or non-aqueous carriers. Aqueous carriers include, without limitation, water, alcohol, saline, and buffered solutions. Examples of non-aqueous carriers include, without limitation, propylene glycol, polyethylene glycol, vegetable oils, and injectable organic esters. Preservatives and other additives such as, for example, antimicrobials, anti-oxidants, chelating agents, inert gases, and the like may also be present. Pharmaceutically acceptable carriers for intravenous administration include solutions containing pharmaceutically acceptable salts or sugars. Intranasal preparations can be presented in a liquid form (e.g., nasal drops or aerosols) or as a dry product (e.g., a powder). Both liquid and dry nasal preparations can be administered using a suitable inhalation device. Nebulised aqueous suspensions or solutions can also be prepared with or without a suitable pH and/or tonicity adjustment.

Detecting PAPSS1 Sequence Variants

PAPSS1 nucleotide sequence variants can be detected, for example, by sequencing exons, introns, 5' untranslated sequences, or 3' untranslated sequences, by performing allele-specific hybridization, allele-specific restriction digests, mutation specific polymerase chain reactions (MSPCR), by single-stranded conformational polymorphism (SSCP) detection (Schafer et al., 1995, *Nat. Biotechnol.* 15:33-39), denaturing high performance liquid chromatography (DHPLC, Underhill et al., 1997, *Genome Res.*, 7:996-1005), infrared matrix-assisted laser desorption/ionization (IR-MALDI) mass spectrometry (WO 99/57318), and combinations of such methods.

Genomic DNA generally is used in the analysis of PAPSS1 nucleotide sequence variants. Genomic DNA is typically extracted from a biological sample such as a peripheral blood sample, but can be extracted from other biological samples, including tissues (e.g., mucosal scrapings of the lining of the mouth or from renal or hepatic tissue). Routine methods can be used to extract genomic DNA from a blood or tissue sample, including, for example, phenol extraction. Alternatively, genomic DNA can be extracted with kits such as the QIAamp® Tissue Kit (Qiagen, Chatsworth, Calif.), Wizard® Genomic DNA purification kit (Promega) and the A.S.A.P.™ Genomic DNA isolation kit (Boehringer Mannheim, Indianapolis, Ind.).

Typically, an amplification step is performed before proceeding with the detection method. For example, exons or introns of the PAPSS1 gene can be amplified then directly sequenced. Dye primer sequencing can be used to increase the accuracy of detecting heterozygous samples.

Allele specific hybridization also can be used to detect sequence variants, including complete haplotypes of a mammal. See, Stoneking et al., 1991, *Am. J. Hum. Genet.* 48:370-382; and Prince et al., 2001, *Genome Res.*, 11(1): 152-162. In practice, samples of DNA or RNA from one or more mammals can be amplified using pairs of primers and the resulting amplification products can be immobilized on a substrate (e.g., in discrete regions). Hybridization conditions are selected such that a nucleic acid probe can specifically bind to the sequence of interest, e.g., the variant nucleic acid sequence. Such hybridizations typically are performed under high stringency as some sequence variants include only a single nucleotide difference. High stringency conditions can include the use of low ionic strength solutions and high temperatures for washing. For example, nucleic acid molecules can be hybridized at 42° C. in 2×SSC (0.3M NaCl/0.03 M sodium citrate/0.1% sodium dodecyl sulfate (SDS) and washed in 0.1×SSC (0.015M NaCl/0.0015 M sodium citrate), 0.1% SDS at 65° C. Hybridization conditions can be adjusted to account for unique features of the nucleic acid molecule, including length and sequence composition. Probes can be labeled (e.g., fluorescently) to facilitate detection. In some embodiments, one of the primers used in the amplification reaction is biotinylated (e.g., 5' end of reverse primer) and the resulting biotinylated amplification product is immobilized on an avidin or streptavidin coated substrate.

Allele-specific restriction digests can be performed in the following manner. For nucleotide sequence variants that introduce a restriction site, restriction digest with the particular restriction enzyme can differentiate the alleles. For PAPSS1 sequence variants that do not alter a common restriction site, mutagenic primers can be designed that introduce a restriction site when the variant allele is present or when the wild type allele is present. A portion of PAPSS1 nucleic acid can be amplified using the mutagenic primer and a wild type primer, followed by digest with the appropriate restriction endonuclease.

Certain variants, such as insertions or deletions of one or more nucleotides, change the size of the DNA fragment encompassing the variant. The insertion or deletion of nucleotides can be assessed by amplifying the region encompassing the variant and determining the size of the amplified products in comparison with size standards. For example, a region of PAPSS1 can be amplified using a primer set from either side of the variant. One of the primers is typically labeled, for example, with a fluorescent moiety, to facilitate sizing. The amplified products can be electrophoresed through acrylamide gels with a set of size standards that are labeled with a fluorescent moiety that differs from the primer.

PCR conditions and primers can be developed that amplify a product only when the variant allele is present or only when the wild type allele is present (MSPCR or allele-specific PCR). For example, patient DNA and a control can be amplified separately using either a wild type primer or a primer specific for the variant allele. Each set of reactions is then examined for the presence of amplification products using standard methods to visualize the DNA. For example, the reactions can be electrophoresed through an agarose gel and the DNA visualized by staining with ethidium bromide or other DNA intercalating dye. In DNA samples from heterozygous patients, reaction products would be detected in each reaction. Patient samples containing solely the wild type allele would have amplification products only in the reaction using the wild type primer. Similarly, patient samples containing solely the variant allele would have amplification products only in the reaction using the variant primer. Allele-specific PCR also can be performed using allele-specific primers that introduce priming sites for two universal energy-transfer-labeled primers (e.g., one primer labeled with a green dye such as fluoroscein and one primer labeled with a red dye such as sulforhodamine). Amplification products can be analyzed for green and red fluorescence in a plate reader. See, Myakishev et al., 2001, *Genome* 11(11):163-169.

Mismatch cleavage methods also can be used to detect differing sequences by PCR amplification, followed by hybridization with the wild type sequence and cleavage at points of mismatch. Chemical reagents, such as carbodiimide or hydroxylamine and osmium tetroxide can be used to modify mismatched nucleotides to facilitate cleavage.

Alternatively, PAPSS1 variants can be detected by antibodies that have specific binding affinity for variant PAPSS1 polypeptides. Variant PAPSS1 polypeptides can be produced in various ways, including recombinantly, as discussed above. Host animals such as rabbits, chickens, mice, guinea pigs, and rats can be immunized by injection of a PAPSS1 variant polypeptide. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin, and dinitrophenol. Polyclonal antibodies are heterogeneous populations of antibody molecules that are contained in the sera of the immunized animals. Monoclonal antibodies, which are homogeneous populations of antibodies to a particular antigen, can be prepared using a PAPSS1 variant polypeptide and standard hybridoma technology. In particular, monoclonal antibodies can be obtained by any technique that provides for the production of antibody molecules by continuous cell lines in culture such as described by Kohler et al., Nature, 256:495 (1975), the human B-cell hybridoma technique (Kosbor et al., Immunology Today, 4:72 (1983); Cole et al., Proc. Natl. Acad. Sci USA, 80:2026 (1983)), and the EBV-hybridoma technique (Cole et al., Monoclonal Antibodies and Cancer Therapy, Alan R. Liss, Inc., pp. 77-96 (1983). Such antibodies can be of any immunoglobulin class including IgG, IgM, IgE, IgA, IgD and any subclass thereof. The hybridoma producing the monoclonal antibodies of the invention can be cultivated in vitro and in vivo.

Antibody fragments that have specific binding affinity for a PAPSS1 variant polypeptide can be generated by known techniques. For example, such fragments include but are not limited to F(ab')2 fragments that can be produced by pepsin digestion of the antibody molecule, and Fab fragments that can be generated by reducing the disulfide bridges of F(ab')2 fragments. Alternatively, Fab expression libraries can be constructed. See, for example, Huse et al., Science, 246:1275 (1989). Once produced, antibodies or fragments thereof are tested for recognition of PAPSS variant polypeptides by standard immunoassay methods including ELISA techniques, radioimmunoassays and Western blotting. See, Short Protocols in Molecular Biology, Chapter 11, Green Publishing Associates and John Wiley & Sons, edited by Ausubel et al., 1992.

Methods of the Invention

As a result of the present invention, it is now possible to determine PAPS synthesis status of a mammal (e.g., a human subject) as well as to determine if particular SNPs are linked to a particular disease or clinical condition. In some embodiments, for example, it is possible to determine whether a mammal is predisposed (i.e., has a relative greater risk) to joint diseases, hormone dependent diseases, or cancer. "PAPS synthesis status" refers to the ability of a mammal to synthesize PAPS. Additional risk factors including, for example, family history and other genetic factors can be considered when determining risk. Predisposition to joint diseases, hormone dependent diseases, or cancer can be determined based on the presence or absence of a single PAPSS1 sequence variant or based on a variant profile. "Variant profile" refers to the presence or absence of a plurality (i.e., two or more sequence variants) of PAPSS1 nucleotide sequence variants or PAPSS1 amino acid sequence variants. For example, a variant profile can include the complete PAPSS1 haplotype of the mammal or can include the presence or absence of a set of common non-synonymous SNPs (i.e., single nucleotide substitutions that alter the amino acid sequence of a PAPSS1 polypeptide). In one embodiment, the variant profile includes detecting the presence or absence of two or more non-synonymous SNPs (e.g., 2, 3, 4 or more non-synonymous SNPs and combinations thereof) described above. There may be ethnic-specific pharmacogenetic variation, as certain of the nucleotide and amino acid sequence variants described herein were detected solely in a particular ethnic group (i.e., a group of African-American subjects or a group of Caucasian subjects). In addition, the variant profile can include detecting the presence or absence of any type of PAPSS1 SNP together with any other PAPSS1 SNP (i.e., a polymorphism pair or groups of polymorphism pairs). Such polymorphism pairs include, without limitation, those pairs described in Tables 4 and 5. Further, the variant profile can include detecting the presence or absence of any PAPSS SNP together with any SNP from another PAPSS. For example, a variant profile can include SNPs from both PAPSS1 and PAPSS2.

Articles of Manufacture

Articles of manufacture of the invention include populations of isolated PAPSS1 nucleic acid molecules or PAPSS1 polypeptides immobilized on a substrate. Suitable substrates provide a base for the immobilization of the nucleic acids or polypeptides, and in some embodiments, allow immobilization of nucleic acids or polypeptides into discrete regions. In embodiments in which the substrate includes a plurality of discrete regions, different populations of isolated nucleic acids or polypeptides can be immobilized in each discrete region. Thus, each discrete region of the substrate can include a different PAPSS1 nucleic acid or PAPSS1 polypeptide sequence variant. Such articles of manufacture can include two or more sequence variants of PAPSS1, or can include all of the sequence variants known for PAPSS1. For example, the article of manufacture can include two or more of the sequence variants identified herein and one or more other PAPSS1 sequence variants, such as nucleic acid variants that result in amino acid changes of Leu270Phe and Gln355Arg. Furthermore, nucleic acid molecules containing sequence variants for other PAPS synthetases, such as PAPSS2, can be included on the substrate.

Suitable substrates can be of any shape or form and can be constructed from, for example, glass, silicon, metal, plastic, cellulose, or a composite. For example, a suitable substrate can include a multiwell plate or membrane, a glass slide, a chip, or polystyrene or magnetic beads. Nucleic acid molecules or polypeptides can be synthesized in situ, immobilized directly on the substrate, or immobilized via a linker, including by covalent, ionic, or physical linkage. Linkers for immobilizing nucleic acids and polypeptides, including reversible or cleavable linkers, are known in the art. See, for example, U.S. Pat. No. 5,451,683 and WO98/20019. Immobilized nucleic acid molecules are typically about 20 nucleotides in length, but can vary from about 10 nucleotides to about 1000 nucleotides in length.

In practice, a sample of DNA or RNA from a subject can be amplified, the amplification product hybridized to an article of manufacture containing populations of isolated nucleic acid molecules in discrete regions, and hybridization can be detected. Typically, the amplified product is labeled to facilitate detection of hybridization. See, for example, Hacia et al., Nature Genet., 14:441-447 (1996); and U.S. Pat. Nos. 5,770,722 and 5,733,729.

The invention will be further described in the following examples, which do not limit the scope of the invention described in the claims.

EXAMPLES

Example 1

Methods and Materials

PCR Amplification and DNA Sequencing: DNA samples from 60 Caucasian-American and 60 African-American subjects were obtained from the Coriell Institute Cell Repository (Camden, N.J.). These samples had been anonymized, and written informed consent had been obtained from all donors for the use of their DNA for this purpose. All experiments were reviewed and approved by the Mayo Clinic Institutional Review Board. Twelve PCR reactions were performed with each DNA sample to amplify all PAPSS1 exons and splice junctions. The amplicons were then sequenced using dye-primer sequencing chemistry to facilitate the identification of heterozygous bases (Chadwick et al. *Biotechniques* 20:676-683 (1996)). To make that possible, universal M13 sequencing tags were added to the 5'-ends of each forward and reverse primer. All forward primers contained the M13 forward sequence (5'-TGTAAAACGACGGCCAGT-3'; SEQ ID NO:15), and all reverse primers contained the M13 reverse sequence (5'-CAGGAAACAGCTATGACC-3'; SEQ ID NO:16). The sequences and locations of each primer within the gene are listed in Table 1. "F" represents forward; "R", reverse; "U", upstream; "D", downstream; "I", intron; "FR", flanking region; and "UTR", untranslated region. The locations of primers within the gene were chosen to avoid repetitive sequence as well as regions of known homology between the two PAPSS genes.

Amplifications were performed with AmpliTaq Gold DNA polymerase (Perkin Elmer, Foster City, Calif.) using a "hot start" to help ensure amplification specificity. The amplifications were conducted as follows: exon 1-35 cycles of 30 seconds at 94° C. and 2 minutes at 72° C.; exon 2-35 cycles of 30 seconds at 94° C., 30 seconds at 65° C., and 2 minutes at 72° C.; exons 3 and 4-35 cycles of 30 seconds at 94° C., 30 seconds at 60° C., and 2 minutes at 72° C.; exon 5-35 cycles of 30 seconds at 94° C., 20 seconds at 64° C., and 1 minute at 72° C.; exon 6-35 cycles of 30 seconds at 94° C., 20 seconds at 60° C., and 2 minutes at 72° C.; exons 7 and 8-20 cycles of 30 seconds at 94° C., 30 seconds at 55° C., and 45 seconds at 72° C., followed by 20 cycles of 30 seconds at 94° C., 30 seconds at 70° C., and 45 seconds at 72° C.; exons 9, 10 and 11-35 cycles of 30 seconds at 94° C., 30 seconds at 65° C., and 2 minutes at 72° C.; and exon 12-35 cycles of 30 seconds at 94° C., 30 seconds at 60° C., and 2 minutes at 72° C.

Amplicons were sequenced in the Mayo Molecular Biology Core Facility with an ABI 377 DNA sequencer using BigDye™ (Perkin Elmer) dye-primer sequencing chemistry. Both DNA strands were sequenced in all cases. Since the 5'-flanking region of PAPSS1 near the site of transcription initiation is very GC-rich, multiple attempts to obtain high quality sequencing chromatograms for that region of the gene were unsuccessful. Finally, to exclude PCR-induced artifacts, independent amplification followed by DNA sequencing was performed for all samples in which a SNP was only observed once among the samples resequenced. DNA sequence chromatograms were analyzed using the PolyPhred 3.0 (Nickerson et al. *Nucl. Acids Res.* 25:2745-2751 (1997)) and Consed 8.0 (Gordon et al. *Genome Res.* 8:195-202 (1998)) programs developed by the University of Washington (Seattle, Wash.). The University of Wisconsin GCG software package, Version 10, was also used to analyze nucleotide sequence. GenBank accession numbers for the PAPSS1 reference sequences were AF097710 to AF097721 (Xu et al. 2000, supra).

Recombinant PAPSS1 Expression Constructs and Allozyme Expression: PAPSS1 cDNA sequences for the two non-synonymous cSNPs that were observed during the resequencing experiments were created using the Quick-Change Site-Directed Mutagenesis kit (Stratagene, La Jolla, Calif.), with the wild type PAPSS1 cDNA open reading frame (ORF) in the pUni/V5-His-TOPO (pUni) vector (Invitrogen) as template. Specifically, the full-length wild type ORF (GenBank accession number AF105227) was amplified using human brain Marathon-Ready cDNA (Clontech) as template with primer pair F1 (5'-GAGGAG GAATTCATGGAGATCCCCGGGAGCTTG-3'; SEQ ID NO:17) and R1982 (5'-GATAAGGAATTCTTAGGAA GCATGTCCAGACAGACAC; SEQ ID NO:18). The resultant PAPSS1 cDNA was subdloned into pUni, a vector that is only 2.3 kilobases in length, so it is well suited for performing "circular PCR" during site-directed mutagenesis. Site-directed mutagenesis was performed using internal primers that contained the variant nucleotide sequences. Since both F1 and R1982 contained EcoRI sites (underlined in the sequences), the PAPSS1 cDNA inserts in pUni could be easily excised and re-ligated into the eukaryotic expression vector p91023(b) (Wong et al. *Science* 228:810-815 (1985)). The sequences of inserts in p91023(b) were confirmed by completely sequencing both strands.

Expression constructs for the wild type and variant PAPSS1 sequences were transfected into COS-1 and HEK293 cells using the TransFast™ reagent (Promega), with a 1:1 charge ratio. pSV-β-Galactosidase (Promega) was co-transfected as an internal control to make it possible to correct for transfection efficiency. The COS-1 and HEK293 cells were harvested after 48 hours and were homogenized with a Polytron homogenizer (Brinkmann Instruments, Westbury, N.Y.) in 25 mM potassium phosphate buffer, pH 7.8 that contained 1 mM dithiothreitol (DTT) and 1 mM EDTA. Cell homogenates were centrifuged at 15,000×g for 15 minutes, and the resultant supernatant preparations were used for enzyme assays and substrate kinetic studies.

PAPSS1 Enzyme Activity: PAPSS1 activity was measured with a coupled radiochemical assay. See Xu et al. 2001, supra. Briefly, PAPS is generated from ATP and $Na_2SO_4$ in a PAPSS1-catalyzed reaction. The generated PAPS is then used as a substrate for the SULT1E1-catalyzed sulfate conjugation of [2,4,6,7-$^3$H]estradiol, a radioactively labeled sulfate acceptor substrate. The cell homogenate preparations of recombinant PAPSS1 allozymes described above were used for the activity studies without any further purification. The protein concentration of each recombinant protein preparation was determined by the dye-binding method of Bradford (*Anal. Biochem.* 72:248-254 (1976)) with bovine serum albumin as a standard.

PAPS synthesis was catalyzed by recombinant wild-type PAPSS1 or PAPSS1 allozymes (present in the cell homogenate preparations described above) in the presence of 1 mM ATP, 4 mM $Na_2SO_4$, 1 mM $MgCl_2$, and 2 mM DTT in 60 mM glycine-NaOH buffer, pH 8.6. "Blank" samples included the same quantity of COS-1 or HEK293 15,000×g supernatant from cells that had been transfected with "empty" p91023(b) expression vector to make it possible to correct for endogenous activity. The endogenous COS-1 cell activity was at most 10% of that assayed for the recombinant enzyme under optimal conditions. Reaction mixtures were incubated at 37° C. for 20 minutes, and then terminated by heating at 100° C. for 1 minute. An aliquot from this PAPS-generating reaction was then added to a second, coupled reaction containing recombinant human SULT1E1 isolated from COS-1 cells transfected with a SULT1E1 expression construct (see Aksoy et al., *Biochem. Biophys. Res. Commun.*, 200:1621-1629 (1994)). The coupled reaction also included 27 nM [2,4,6,7-$^3$H]estradiol, 8 mM DTT and 1.25 mM $MgCl_2$ in 10 mM potassium phosphate buffer, pH 6.5. The second, SULT1E1-catalyzed reactions were incubated at 37° C. for 20 minutes, and then terminated by the addition of KOH, followed by organic solvent extraction performed with chloroform. Radioactivity of the sulfate conjugated [2,4,6,7-$^3$H]estradiol in the aqueous phase after organic solvent extraction was then measured in a liquid scintillation counter. PAPSS activities of recombinant PAPSS1 allozymes were compared after correction for transfection efficiency by measuring the activity of cotransfected β-galactosidase. β-Galactosidase activity in the COS-1 and HEK293 cell preparations was measured with the β-Galactosidase Assay System (Promega) as described by the manufacturer.

Estimating Apparent $K_m$ Values: To estimate apparent $K_m$ values of PAPSS1 for the two reaction cosubstrates, a series of 8 ATP (0.125-4 mM) and 9 $Na_2SO_4$ (0.125-16 mM) concentrations were tested with the recombinant allozymes. When ATP was the varied substrate, the concentration of $Na_2SO_4$ was 4 mM, and when $Na_2SO_4$ was the varied substrate, the concentration of ATP was 1 mM. Blanks for each substrate concentration were included by assaying COS-1 cell cytosol after transfection with empty p91023(b) vector. These data were fitted to a series of kinetic models, and the most appropriate model is selected on the basis of the dispersion of residuals and a determination of whether the F-test showed a significant reduction (P<0.05) in the residual sums of squares. Apparent $K_m$ values were calculated using the method of Wilkinson with a computer program written by Cleland. Wilkinson supra; and Cleland supra.

Western Blot Analysis: Quantitative Western blot analysis was performed with recombinant PAPSS1 allozymes after expression in COS-1 cells. Since all constructs included an N-terminal His-tag, anti-His monoclonal antibodies (Invitrogen) were used to measure levels of immunoreactive PAPSS1 protein with the ECL detection system (Amersham Pharmacia, Piscataway, N.J.). The quantity of COS-1 cell preparation loaded on the gel for each allozyme was adjusted to achieve equal quantities of β-galactosidase activity, i.e., gel loading was adjusted to correct for transfection efficiency. The AMBIS Radioanalytic Imaging System, Quant Probe Version 4.31 (Ambis, Inc., San Diego, Calif.) was used to quantitate immunoreactive protein in each lane, and those data were expressed as a percentage of the intensity of the wild type PAPSS1 band on the gel.

Data Analysis: Statistical comparisons of data were performed by ANOVA with the StatView program, version 4.5 (Abacus Concepts, Inc., Berkeley, Calif.). Linkage analysis was performed after all DNA samples had been genotyped at each of the 21 polymorphic sites observed, using the EH program developed by Terwilliger and Ott, *Handbook of Human Genetic Linkage*, The Johns Hopkins University Press, Baltimore, pp. 188-193 (1994). D' values, a quantitative method for reporting linkage data that is independent of allele frequency (Hartl and Clark *Principles of Population Genetics*, 3$^{rd}$ edition, Sinauer Associates, Inc., (Sunderland, Mass.), pp 96-106 (1997); and Hedrick *Genetics of Populations*, 2$^{nd}$ edition, Jones and Bartlett (Sudbury, Mass.), pp. 396-405 (2000)), were then calculated. The genotype data also were used to assign inferred haplotypes using a program based on the E-M algorithm (Long et al. *Am. J. Hum. Genet.* 56:799-810 (1995); and Excoffier and Slatkin *Mol. Biol. Evol.* 12:921-927 (1995)). Unambiguous haplotype assignment also was possible on the basis of genotype for samples that contained no more than one heterozygous polymorphism.

TABLE 1

PCR primers used for resequencing PAPSS1

| Primer Name | Primer Location | Primer Sequence (5' to 3' direction) | SEQ ID NO: |
|---|---|---|---|
| UF(-84) M13 | 5'-FR | TGTAAAACGACGGCCAGTAGCCCCGCCCCGCTCGCTGGCCTG | 19 |
| I1R152 M13 | Intron 1 | CAGGAAACAGCTATGACCGCCCCAGCCGGGAGGCGCCG | 20 |
| I1F(-103) M13 | Intron 1 | TGTAAAACGACGGCCAGTGCTTTTGGCATGTTACATAG | 21 |
| I2R116 M13 | Intron 2 | CAGGAAACAGCTATGACCTCGTGATGCTCCAAATACAAG | 22 |
| I2F(-67) M13 | Intron 2 | TGTAAAACGACGGCCAGTAAAGTATTACTACATAGTTATCC | 23 |
| I3R119 M13 | Intron 3 | CAGGAAACAGCTATGACCAGCTGGGGAGGAGTAGAGTTA | 24 |
| I3F(-102) M13 | Intron 3 | TGTAAAACGACGGCCAGTTTTCCCACTAAATTGGATGA | 25 |
| I4R231 M13 | Intron 4 | CAGGAAACAGCTATGACCCTCCCGAGCCCCAA | 26 |
| I4F(-159) M13 | Intron 4 | TGTAAAACGACGGCCAGTTAATTAGAAATCTCCCAAGAA | 27 |
| I5R179 M13 | Intron 5 | CAGGAAACAGCTATGACCACGGTGCTCCCCACAACA | 28 |
| I5F(-280) M13 | Intron 5 | TGTAAAACGACGGCCAGTTGAGGCCACCTCTCATTTGT | 29 |
| I6R192 M13 | Intron 6 | CAGGAAACAGCTATGACCATGGTAACTTGGGAACATGGTTG | 30 |
| I6F(-143) M13 | Intron 6 | TGTAAAACGACGGCCAGTTCTTTGTTAGTTTGGTATA | 31 |

TABLE 1-continued

PCR primers used for resequencing PAPSS1

| Primer Name | Primer Location | Primer Sequence (5' to 3' direction) | SEQ ID NO: |
|---|---|---|---|
| I7R155 M13 | Intron 7 | CAGGAAACAGCTATGACCCTTAAATAAAGTGTTCGGTA | 32 |
| I7F(-109) M13 | Intron 7 | TGTAAAACGACGGCCAGTTACAGCCTTTTATTATTTG | 33 |
| I8R167 M13 | Intron 8 | CAGGAAACAGCTATGACCCCAAAATGACAAGAG | 34 |
| I8F(-93) M13 | Intron 8 | TGTAAAACGACGGCCAGTAGCTTACAACGACTGTATTTAGC | 35 |
| I9R155 M13 | Intron 9 | CAGGAAACAGCTATGACCACCCAGGCTAGTTTTGATTG | 36 |
| I9F(-68) M13 | Intron 9 | TGTAAAACGACGGCCAGTTTGCGTATCCTTTGGAAAG | 37 |
| I10R70 M13 | Intron 10 | CAGGAAACAGCTATGACCTGCCCCTAGCATCCA | 38 |
| I10F(-148) M13 | Intron 10 | TGTAAAACGACGGCCAGTCTGGCTTCCCAGGATGATA | 39 |
| I11R146 M13 | Intron 11 | CAGGAAACAGCTATGACCGGGAAATTACTTTTCTGGGTTTACC | 40 |
| I11F(-91) M13 | Intron 11 | TGTAAAACGACGGCCAGTTTTGTCTAATATGAACAGAAGG | 41 |
| R2005 M13 | 3'-UTR | CAGGAAACAGCTATGACCAAGTTAAGGAAAATGGTCTG | 42 |

Underlined nucleotides indicate M13 tag

Example 2

PAPSS1 Polymorphisms

Twelve separate PCR amplifications were performed for each of the 120 DNA samples studied. However, 2 of the samples from African-American subjects consistently failed to amplify with any of the primer pairs. The subsequent data thus include only 58 samples from African-Americans. As a result, the DNA resequencing experiments involved the analysis, in total, of approximately 1.1 million base pairs of sequence. All PCR amplicons were sequenced on both strands, making it possible to verify the presence of polymorphisms using data from the complimentary strand. A total of 21 polymorphisms were observed, including 20 SNPs and one insertion event (Table 2). Polymorphisms in exons, untranslated regions (UTR), and flanking regions (FR) are numbered relative to the adenine in the PAPSS1 translation initiation codon (ATG, adenine is +1). Polymorphisms in introns are numbered separately, either as positive numbers relative to the guanine in the splice donor site (GT, guanine is +1), or as negative numbers relative to the guanine in the splice acceptor site (AG, guanine is −1).

Variant allele frequencies ranged from 0.8% to 53.6%, with striking differences between the African-American and Caucasian-American subjects. Nineteen polymorphisms were observed in 58 DNA samples from African-American subjects, while only 13 were found in the 60 samples from Caucasian-American subjects. The overall number of PAPSS1 polymorphisms per kilobase of sequence in the 118 samples studied (4.3 polymorphisms/kilobase) was close to that (4.6/kilobase) observed in similar studies of other human genes (Halushka et al., Nature Genet., 22:239-247 (1999)). Seven of the SNPs were within the coding-region (cSNPs), and two of those cSNPs—located in exons 8 and 11—were nonsynonymous and resulted in the in the amino acid alterations Arg333Cys and Glu531Gln. The Arg333Cys polymorphism had a frequency of 2.5% in Caucasians but was not observed in DNA from African-American subjects. The Glu531Gln polymorphism was rare, with only one copy of the variant allele in a single African-American DNA sample. Of the 21 polymorphisms, three were observed only once in the 236 alleles that were successfully resequenced. To exclude artifacts introduced by PCR-dependent misincorporation, independent amplifications were performed and the amplicons were sequenced in all cases in which a polymorphism was observed only once among the DNA samples studied. The proximal 5'-flanking region of PAPSS1 is very GC rich, so we were unable to resequence that region of the gene using either dye primer or dye terminator sequencing chemistry.

TABLE 2

Human PAPSS1 sequence variants

| | | Nucleotide | | | Frequency of Variant | |
|---|---|---|---|---|---|---|
| Position | Location | Wild Type Allele | Variant Allele | Altered Amino Acid | African Americans | Caucasian Americans |
| −44 | 5'-UTR | C | T | | 0.091 | 0.008 |
| 19 | Exon 1 | C* | T | | 0.254 | 0.583 |

TABLE 2-continued

Human PAPSS1 sequence variants

| | | Nucleotide | | | Frequency of Variant | |
|---|---|---|---|---|---|---|
| Position | Location | Wild Type Allele | Variant Allele | Altered Amino Acid | African Americans | Caucasian Americans |
| 36 | Exon 1 | G | A | | 0.254 | 0.058 |
| I1(107) | Intron 1 | C | G | | 0.536 | 0.067 |
| I1(-34) | Intron 1 | G** | A | | 0.272 | 0.593 |
| I2(55) | Intron 2 | C | T | | 0.018 | 0.000 |
| I3(36) | Intron 3 | A | G | | 0.138 | 0.000 |
| I4(18) | Intron 4 | C | T | | 0.094 | 0.008 |
| I4(86) | Intron 4 | — | 5'-AGTGTTAGA-3' | | 0.215 | 0.033 |
| I5(143) | Intron 5 | G | C | | 0.103 | 0.000 |
| 675 | Exon 6 | T | C | | 0.000 | 0.008 |
| 963 | Exon 8 | C | T | | 0.211 | 0.246 |
| 997 | Exon 8 | C | T | Arg333Cys | 0.000 | 0.025 |
| I8(-14) | Intron 8 | G | C | | 0.009 | 0.000 |
| 1260 | Exon 10 | A | G | | 0.009 | 0.017 |
| I10(12) | Intron 10 | G | T | | 0.017 | 0.000 |
| I10(125) | Intron 10 | A | G | | 0.017 | 0.000 |
| I10(-32) | Intron 10 | C | G | | 0.052 | 0.254 |
| I10(-7) | Intron 10 | A | G | | 0.017 | 0.000 |
| 1591 | Exon 11 | G | C | Glu531Gln | 0.009 | 0.000 |
| 1945 | 3'-UTR | G | A | | 0.043 | 0.254 |

*C at this position is considered to be wild type in African Americans, while T at this position is considered to be wild type in Caucasian Americans.
**G at this position is considered to be wild type in African Americans, while A at this position is considered to be wild type in Caucasian Americans.

Example 3

Linkage Disequilibrium and Haplotype Analysis

Linkage disequilibrium analysis was performed after all of the DNA samples had been genotyped at each of the 21 polymorphic sites. 12 polymorphisms with allele frequencies greater than 2.5% were chosen for inclusion in this analysis, because there was inadequate statistical power for the analysis of less common polymorphisms. Pairwise combinations of these 12 polymorphisms were tested for linkage disequilibrium using the EH program developed by Terwilliger and Ott, supra. The output of this program was used to calculate D' values, a method for reporting linkage data that is independent of sample size (Table 3).

The genotype data were also used for haplotype analysis. In this case, unambiguous haplotype assignment could be made for samples that contained no more than one heterozygous locus. Haplotypes for some of the remaining alleles were inferred from the genotype data as well as the EM probabilities (Table 4). Linkage analysis also was performed by calculating D' values for all possible pairwise combinations of the observed PAPSS1 polymorphisms. D' values reflect the degree of linkage between two loci and can range from (+1.0) when two polymorphisms are maximally positively associated, to (−1.0) when two polymorphisms never occur together (Hartl and Clark supra; and Hedrick supra). PAPSS1 polymorphisms with variant allele frequencies lower than 2.5% were excluded from this analysis because of lack of statistical power. The linkage analysis showed that 11 pairs of polymorphisms were in tight positive linkage, with D' values greater than 0.7 (Table 3).

Twelve unequivocal haplotypes also were identified (Table 4), but a total of 29 and 7 additional haplotypes were inferred for the African-American and Caucasian-American samples, respectively, using the E-M algorithm (Long et al. supra; and Excoffier and Slatkin supra). As shown in Table 4, 59% and 86% of all samples were accounted for based on the unequivocal haplotypes for DNA samples from African-American and Caucasian-American subjects, respectively. The unequivocal haplotypes included two that were common to both ethnic groups, and five each that were ethnic-specific for African-American and Caucasian-American subjects. Initial haplotype designations were made on the basis of encoded amino acid sequence, with all "wild type" sequences designated *1, those with the Cys333 variant designated *2 and—although these haplotypes cannot presently be determined unequivocally—those with the Gln531 variant designated *3. Letter designations then were assigned based on descending allele frequencies, starting with the African-American samples.

TABLE 3

PAPSS1 linkage disequilibrium analysis

| Polymorphism Pair | | D' Value | |
|---|---|---|---|
| | | African American | Caucasian American |
| −44 | I1(107) | 1.00 | — |
| 19 | I1(−34) | 1.00 | 0.93 |
| 36 | I1(107) | 0.76 | 1.00 |
| 36 | I3(36) | 1.00 | — |
| 36 | 1945 | 1.00 | — |
| I1(107) | I4(18) | 1.00 | — |
| I3(36) | I10(−32) | 0.78 | — |
| I3(36) | 1945 | 1.00 | — |
| 963 | I10(−32) | 1.00 | 1.00 |
| 963 | 1945 | 1.00 | 1.00 |
| I10(−32) | 1945 | 1.00 | 1.00 |

TABLE 4

PAPSS1 haplotype analysis

| Allele Designation | Frequency | | Exon 1 | | | | | | Exon 8 | | Exon 10 |
|---|---|---|---|---|---|---|---|---|---|---|---|
| | AA | CA | 19 | 36 | I1(107) | I1(−34) | I3(36) | 963 | 997 | 1260 | I10(−32) |
| *1A | 0.231 | 0.371 | T | G | C | A | A | C | C | A | C |
| *1B | 0.053 | 0.267 | C | G | C | G | A | C | C | A | C |
| *1C | 0.169 | — | C | G | G | G | A | C | C | A | C |
| *1D | 0.081 | — | C | A | G | G | A | C | C | A | C |
| *1E | 0.031 | — | C | G | G | G | A | T | C | A | C |
| *1F | 0.014 | — | C | G | C | G | A | T | C | A | C |
| *1G | 0.008 | — | C | A | G | G | G | C | C | A | C |
| *1H | — | 0.192 | C | G | C | A | A | T | C | A | G |
| *1I | — | 0.008 | T | G | C | A | A | C | C | G | C |
| *1J | — | 0.008 | T | G | C | G | A | C | C | A | C |
| *1K | — | 0.008 | C | G | C | A | A | C | C | A | C |
| *2A | | 0.008 | T | G | C | A | A | C | T | A | C |

Example 4

Activity of Variant PAPSS1 Polypeptides

Catalytic activity of cell homogenate preparations containing recombinant PAPSS1 allozymes, prepared as described in Example 1, were used to assess catalytic activity. The resulting activities were adjusted to a percentage of the wild type PAPSS1 enzyme activity (Table 5). Arg333Cys exhibited the greatest reduction in enzyme activity (45.3% reduction, or 54.7% of WT activity), with Glu531Gln showing a smaller reduction in enzyme activity (8.3% reduction, or 91.7% of WT activity).

Expression constructs were created for the two PAPSS1 nonsynonymous cSNPs that were observed during the gene resequencing studies, and those constructs were used to transiently transfect COS-1 and HEK293 cells to perform functional genomic studies. After transfection, the COS-1 and HEK293 cell preparations were assayed for PAPSS activity under optimal conditions for the wild type enzyme (Xu et al. 2001, supra). Under these assay conditions (i.e., in the presence of 1 mM ATP and 4 mM $Na_2SO_4$), neither of the variant PAPSS1 allozymes displayed a significant difference in level of PAPSS activity when compared with the wild type allozyme after expression in either COS-1 or HEK293 cells. Specifically, in COS-1 cells, the Cys333 allozyme had 95.8±7.4% (mean±SEM, N=3) of the wild type activity, while the Glu531Gln allozyme had 96.4±8.6% of wild type activity. All of these data were corrected for transfection efficiency.

TABLE 5

Recombinant human PAPSS1 biochemical properties

| Polymorphism | Amino Acid Change | % WT Activity |
|---|---|---|
| C997T | Arg333Cys | 54.7 ± 4.9 |
| G1591C | Glu531Gln | 91.7 ± 5.3 |
| wild type | none | 100 |

Example 5

Recombinant PAPSS1 Substrate Kinetic Studies

Although significant differences in basal levels of PAPSS1 activity were not observed for either of the variant allozymes, it was still possible that alterations in amino acid sequence might change substrate kinetics. Therefore, a series of 8 ATP (0.125-4 mM) and 9 $Na_2SO_4$ (0.03125-8 mM) concentrations were used to study the recombinant wild type, the Arg333Cys and the Glu531Gln variant PAPSS1 allozymes. All three allozymes exhibited allosteric kinetics for ATP (Venkatachalam et al. *J. Biol. Chem.* 273:19311-19320 (1998); and Xu et al. *Pharmacogenetics* 12:11-21(2002)) with very similar apparent $S_{50}$ values (Table 6). However, when $Na_2SO_4$ was the varied cosubstrate, substrate kinetics for the Glu531Gln allozyme differed from those of the wild type and Arg333Cys allozymes. The Glu531Gln allozyme displayed monophasic substrate kinetics for $Na_2SO_4$, while the wild-type and Arg333Cys allozyme had biphasic kinetics for that substrate. In addition, the Glu531Gln variant allozyme had an apparent $K_m$ value for $SO_4^{2-}$ that was more than 5-fold higher than that of either the wild type or the Arg333Cys allozymes.

TABLE 6

PAPSS1 allozyme substrate kinetics

| Substrate | Kinetic Parameter | Wild type | Arg333Cys | Glu531Gln |
|---|---|---|---|---|
| ATP | Kinetic Model | Allosteric | Allosteric | Allosteric |
|  | $S_{50}$ (mM) | 0.566 ± 0.002 | 0.496 ± 0.001 | 0.499 ± 0.000 |
|  | Hill Coefficient | 5.50 ± 0.10 | 5.99 ± 0.23 | 6.25 ± 0.03 |
|  | Vmax (nmol/hr$^{-1}$/mg$^{-1}$) | 163 ± 1.0 | 145 ± 0.8 | 151 ± 0.6 |
| $Na_2SO_4$ | Kinetic Properties | Biphasic | Biphasic | Monophasic |
|  | $K_{m1}$ (mM) | 0.081 ± 0.004 | 0.075 ± 0.001 | 0.496 ± 0.004 |
|  | $V_{max1}$ (nmol/hr$^{-1}$/mg$^{-1}$) | 139 ± 3.9 | 121 ± 0.8 | 126 ± 0.3 |
|  | $K_{m2}$ (mM) | 5.8 ± 0.9 | 4.4 ± 0.2 | N.A. |
|  | $V_{max2}$ (nmol/hr$^{-1}$/mg$^{-1}$) | 83.2 ± 2.8 | 73.1 ± 1.2 | N.A. |

Values are expressed as mean ± SEM (N = 3).
N.A. is "not applicable."

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated PAPSS1 polypeptide, wherein said polypeptide comprises a PAPSS1 amino acid sequence variant relative to the amino acid sequence of SEQ ID NO:14, wherein said amino acid sequence variant is at a residue selected from the group consisting of 333 and 531.

2. The isolated polypeptide of claim 1, wherein said amino acid sequence variant is a cysteine at residue 333 or a glutamine at residue 531.

3. The isolated polypeptide of claim 1, wherein activity of said polypeptide is altered relative to a wild type PAPSS1 polypeptide.

* * * * *